United States Patent [19]

Even-Chen

[11] Patent Number: 5,242,812
[45] Date of Patent: Sep. 7, 1993

[54] METHOD FOR PRODUCTION AND PURIFICATION OF HEPATITIS B VACCINE

[75] Inventor: Zeev Even-Chen, Yavneh, Israel

[73] Assignee: Bio-Technology General Corp., New York, N.Y.

[21] Appl. No.: 790,485

[22] Filed: Nov. 12, 1991

Related U.S. Application Data

[63] Continuation of Ser. No. 480,166, Feb. 14, 1990, abandoned, which is a continuation-in-part of Ser. No. 307,777, Feb. 7, 1989, abandoned.

[51] Int. Cl.$^5$ .................... C07K 3/26; C07K 3/28; C07K 3/20; C07K 15/14
[52] U.S. Cl. ..................... 435/70.3; 424/88; 424/89; 435/69.3; 530/395; 530/412; 530/414; 530/415; 530/416; 530/417; 530/806; 935/65
[58] Field of Search .................. 424/88, 89; 435/70.3, 435/69.3; 530/412, 414, 416, 417, 415, 806; 935/65

[56] References Cited

U.S. PATENT DOCUMENTS

| | | | |
|---|---|---|---|
| 4,349,539 | 9/1982 | Wampler | 424/89 |
| 4,558,011 | 12/1985 | Brzosko et al. | 435/272 |
| 4,738,926 | 4/1988 | Hamada et al. | 435/239 |

OTHER PUBLICATIONS

Lee et al. 1987, Journal of the Chinese Biochemical Society 16(1): 7-14.
Molnar-Kimber et al. 1988, J. Virology 62(2): 407-416.
Zwerner et al. 1979, Methods in Enzymology, vol. 58: 221-229.

Primary Examiner—Keith C. Furman
Attorney, Agent, or Firm—John P. White

[57] ABSTRACT

Processes are provided for producing purified, hepatitis B surface antigen particles in mammalian cells which comprise culturing mammalian cells which produce the particles in a culture medium supplemented with a serum free of high molecular weight contaminant proteins and recovering the purified, hepatitis B surface antigen particles.

Removal of molecules having a molecular weight greater than about $3 \times 10^5$ daltons by prefractionation, for example, allows cells to be grown in culture media containing high levels of fetal calf serum, removes high molecular weight contaminant proteins which may be inhibitory to cell growth and simplifies purification of HBsAg since high molecular weight contaminant proteins are the major contaminants removed by purification processes.

43 Claims, 10 Drawing Sheets

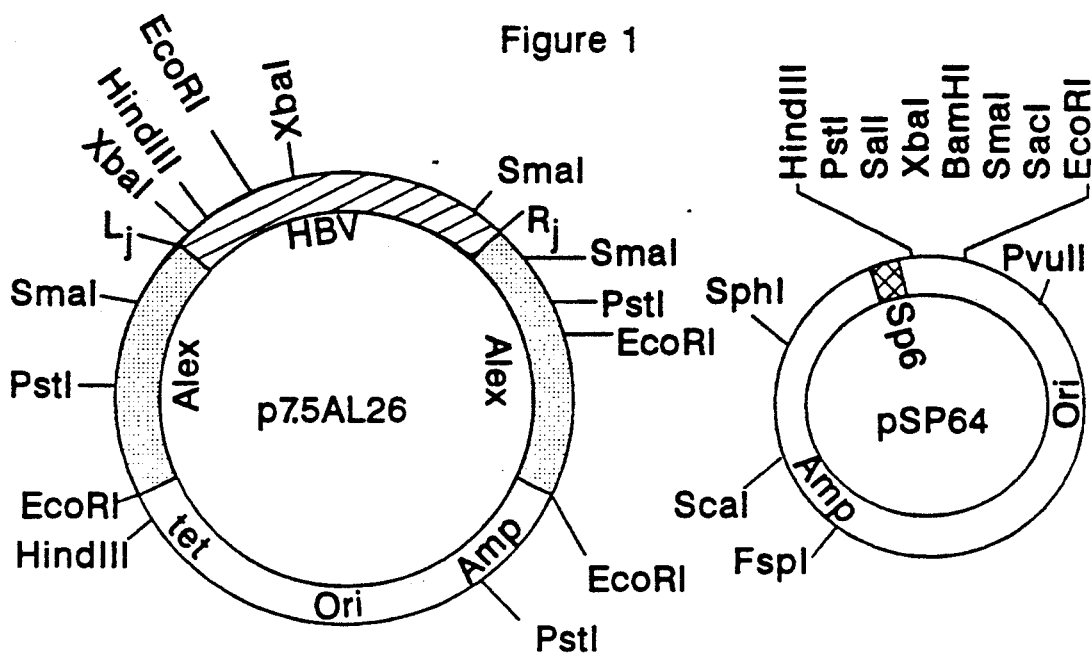
Figure 1
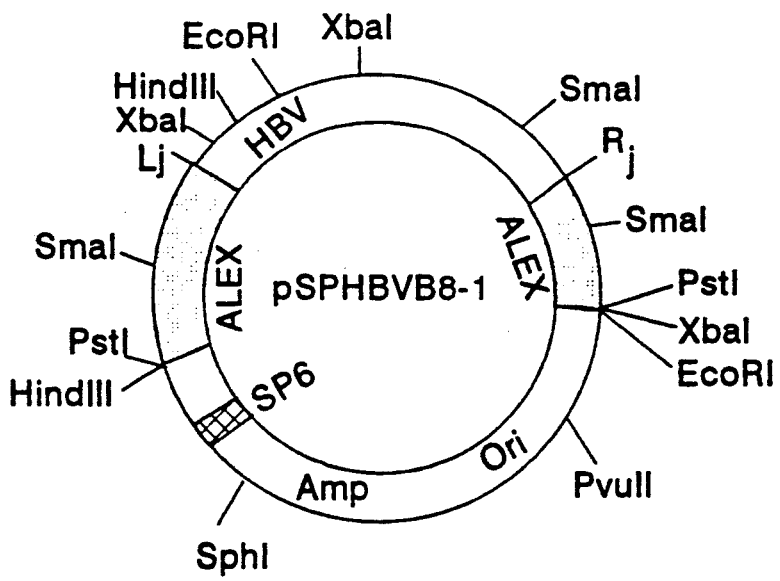

Figure 2
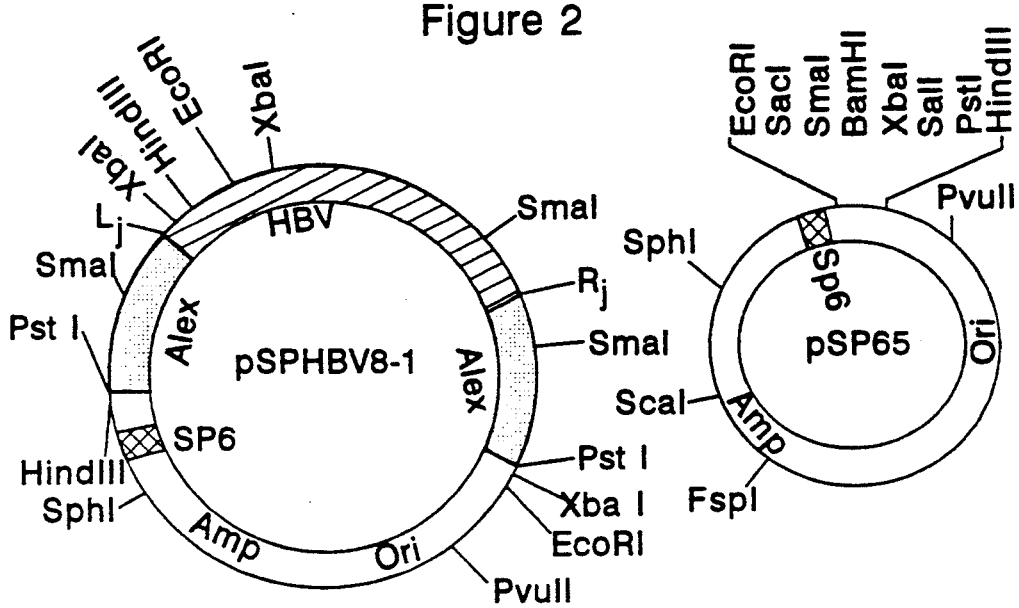
1. EcoRI-XbaI, ISOLATE 500bp FRAGMENT
2. EcoRI-PstI, ISOLATE 2400bp FRAGMENT
1. Xba-PstI, ISOLATE LINEAR FORM
T₄ DNA Ligase
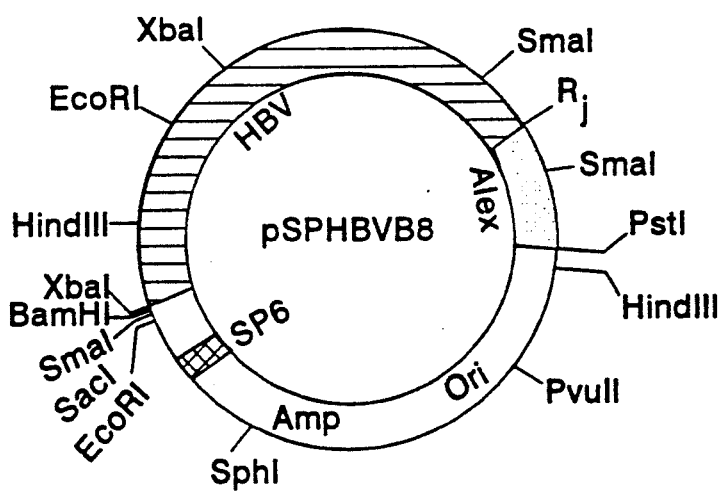

Figure 4
PRODUCTION AND PURIFICATION SCHEME OF HBsAG PARTICLES

STEP 1 — PRODUCTION OF HBsAG PARTICLES IN TISSUE CULTURE SYSTEM USING FCS - SUPPLEMENTED CULTURE MEDIA THAT WAS PREFRACTIONATED ON A PELLICON™ 300,000 MW CUT OFF MEMBRANE - ONLY FILTRATE (PROTEINS< 300,000 MW) IS ADDED TO CELL CULTURE. RETENTATE ON THE MEMBRANE (PROTEINS> 300,000 MW) IS DISCARDED.

STEP 2 — COLLECT CULTURE MEDIA DAILY, POOL AND PURIFY BY FIRST CLARIFYING CRUDE MEDIUM CONTAINING HBsAG PARTICLES ON A PELLICON™ 0.22 MICRON MEMBRANE - ONLY FILTRATE IS PURIFIED FURTHER. RETENTATE (CELLS AND CELL DEBRIS) ON MEMBRANE IS DISCARDED.

STEP 3 — CONCENTRATION OF HBsAG PARTICLES FROM CLARIFIED CRUDE MEDIUM (FILTRATE OF STEP 2) AND DIALYSIS AGAINST PBS ON A PELLICON™ 300,000 MW CUT OFF MEMBRANE - ONLY RETENTATE IS PURIFIED FURTHER (PROTEINS ABOVE 300,000 MW). FILTRATE IS DISCARDED (PROTEINS BELOW 300,000 MW). RETENTATE CONCENTRATED FURTHER ON MINITAN™ 300,000 CUT-OFF MEMBRANE.

STEP 4 — RETENTATE OF STEP 3 IS PURIFIED BY GEL FILTRATION I ON A SEPHACRYL S-400™ COLUMN. FOLLOWED BY CONCENTRATION OF ELUTED HBsAG PEAK FRACTIONS ON MINITAN™ (300,000 MW CUT OFF MEMBRANE).

STEP 5 — CONCENTRATED HBsAG ELUATE OF STEP 4 PURIFIED FURTHER BY GEL FILTRATION II ON SEPHACRYL S-400™ COLUMN, FOLLOWED BY CONCENTRATION OF ELUTED HBsAG PEAK FRACTIONS ON MINITAN™ (300,000 MW CUT OFF MEMBRANE).

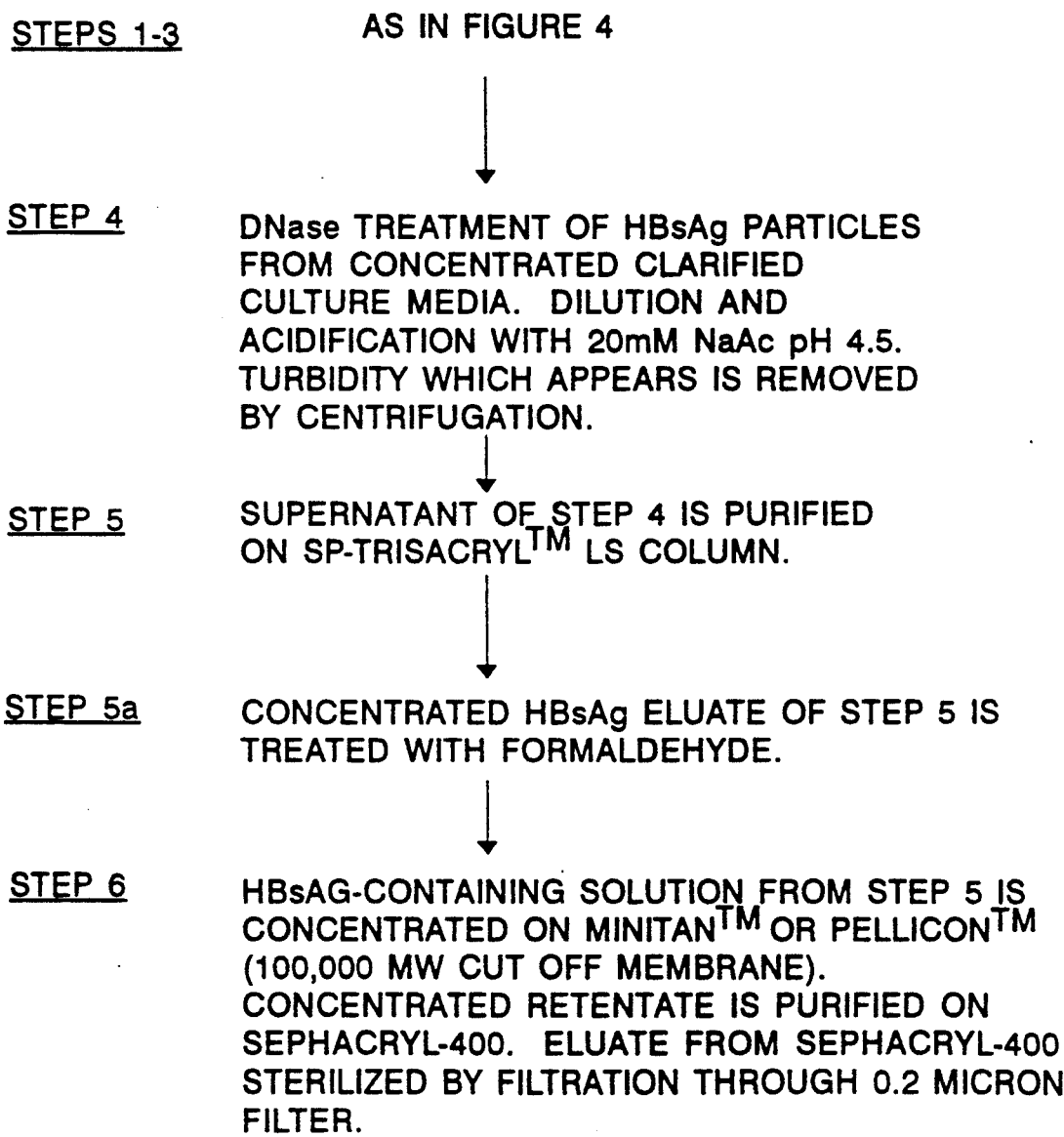

Figure 9

PREFERRED METHOD C FOR PRODUCTION AND

PURIFICATION OF HBsAg PARTICLES

STEPS 1-3     AS IN FIGURE 4

STEP 4     RETENTATE OF STEP 3 IS PURIFIED ON DEAE-FAST FLOW COLUMN. THE FLOW-THROUGH FRACTION IS COLLECTED, DILUTED 1:3 AND ACIDIFIED TO pH 4.5.

STEP 5     ACIDIFIED DILUTED FLOW-THROUGH OF STEP 4 IS PURIFIED ON SP-TRISACRYL® LS COLUMN.

STEP 5a     ELUATE OF STEP 5 IS TREATED WITH FORMALDEHYDE.

STEP 6     DIALYSIS TO REMOVE FORMALDEHYDE ON MINITAN® OR PELLICON® (30K OR 100K MW CUT-OFF MEMBRANE). THE CONCENTRATED RETENTATE IS STERILIZED BY FILTRATION THROUGH 0.2 MICRON FILTER.

METHOD FOR PRODUCTION AND PURIFICATION OF HEPATITIS B VACCINE

This is a continuation of application Ser. No. 480,166, filed Feb. 14, 1990, now abandoned, which is a continuation-in-part of U.S. Ser. No. 307,777, filed Feb. 7, 1989, now abandoned.

BACKGROUND OF THE INVENTION

Hepatitis B virus (HBV) infection is a public health problem of worldwide importance. HBV causes an in-curable and sometimes fatal liver disease which strikes an estimated 20,000 new victims every year in the United States alone. In the Far-East, Africa and Eastern Europe about 10% of the population are chronic carriers of HBV with the result that chronic active hepatitis and liver cirrhosis are major causes of mortality. Further, there is strong evidence that carriers of HBV are far more susceptible to liver cancer, HBV being one of the few viruses known to be involved in human cancer.

Thus, there exists an urgent need for the production of a safe and economically feasible vaccine for protection against HBV infection. Several approaches have been taken to produce such a vaccine. (See Tiollais et al., Nature 317: 489-495 (1985); Patzer et al., Vaccines 85: 261-264, Cold Spring Harbour (1985); and Zuckerman, Infection 13: 61-71, Supplement A (1986) for reviews.)

As described in the above reviews, the basic component of all the vaccines that have been produced is the Hepatitis B surface antigen (HBsAg). It was originally isolated from the plasma of chronic sufferers of HBV infection and employed as an effective vaccine against HBV infection.

HBsAg in the plasma of HBV-infected carriers is present both in the 42 nm HBV infectious viral particles (Dane Particles) and in the form of a non-infectious 22 nm particle which is free of HBV-DNA and other HBV structural proteins. These 22 nm particles are overproduced in both HBV chronic human carriers or during HBV viremia. These 22 nm particles are secreted by HBV transformed hepatoma cell lines.

The 22 nm HBsAg particles, which are highly immunogenic are composed of six related proteins: (a) the major proteins P-24, non-glycosylated form of molecular weight 24,000 daltons (24K) and GP-27, the glycosylated form of P-24, of molecular weight 27,000 daltons (27K). These are encoded by the S region of the HBV genome, and have 226 amino acids; (b) the minor proteins GP-33, a single glycosylated form of molecular weight 33,000 daltons (33K) and GP-36, a double glycosylated form of molecular weight 36,000 daltons (36K). These are encoded by the Pre-S2 and S region of the HBV genome and have 281 amino acids (226 S region +55 Pre-S2 region); (c) the minor proteins P-39, a non-glycosylated form and GP-42, a glycosylated form of P-39 having respective molecular weights of 39,000 and 42,000 daltons (39K, 42K). These are encoded by the Pre-S1, Pre-S2 and S region of the HBV genome and have between 389 and 400 amino acids (226 S +55 Pre-S2 +[108-119]Pre-S1). Thus, all the proteins of the HBsAg 22 nm particles are encoded in the same uninterrupted sequence of HBV genome DNA, their final form depending on where gene expression (transcription and translation) was initiated and whether and to what extent they were glycosylated post-translationally.

22 nm HBsAg particles can be assembled from P-24/GP-27 (S region) independently of Pre-S2 and Pre-S1 products. Recently, it has been shown that the Pre-S2 specific proteins, GP-33 and GP-36, and the Pre-S1 specific proteins, GP-39 and GP-42, have antigenic determinants independent of P-24 and result in an enhanced immunogenicity when present in HBsAg 22 nm particles.

Further, when the Pre-S2 and Pre-S1 proteins are present the 22 nm HBsAg particles have the ability to bind polymerized human serum albumin which is directly related to the ability of HBV viral particles being able to bind target cells during HBV infection. Thus, HBsAg particles containing both the Pre-S and the S region protein determinants can be employed as a vaccine that will elicit a response to neutralize viral particles and to prevent such particles from infecting target cells. In this way, such a vaccine offers effective long term protection against HBV infection (for example, see Persing et al., Proc. Natl. Acad. Sci. USA 82: 3440-3444 (1985); Neurath et al., Nature 315: 154-156 (1985); Neurath et al., Cell 46: 429-436 (1986); petit et al., Mol. Immunol. 23: 511-523 (1986); and Milich et al., J. Immunol. 137: 315-322 (1986).

Methods of HBsAg Vaccine Production and Vaccines Produced by These Methods

1) Blood Plasma Derived Vaccines

In general the original HBsAg vaccines approved for use and employed in immunization programs were derived from the plasma of chronic carriers of HBV. The following are examples of the methods of production of plasma-derived vaccine:

(a) The HEPTAVAX B vaccine produced by Merck, Sharp and Dohme (see review Hilleman et al., J. Infection 7: 3-8, Supplement I (1983);

(b) The HEVAC B vaccine produced by the Pasteur Institute (see review Adamowicz et al., Vaccine 209-214 (1984); and U.S. Pat. No. 4,335,214 issued Jun. 15, 1982.

Both of the above methods are claimed to give plasma-derived HBsAg 22 nm particles of very high purity and free of infectious contaminants and thus safe for use as human vaccines. Key steps used in these methods are however both time consuming and expensive, as they involve polyethylene glycol (PEG) or ammonium sulphate fractionations and subsequent ultracentrifugations in sucrose and caesium chloride gradients. Other more rapid and cheaper methods for producing plasma-derived HBsAg vaccine have been described, but commonly include steps of polyethylene glycol (PEG) or ammonium sulphate fractionation, isopycnic separations using ultra-centrifugation, and chromatographic separations on a variety of chromatographic resins. All of these methods, however, are expensive and time consuming resulting in a high cost for human plasma-derived vaccines (see review in "Hepatitis B Vaccine" Maupas and Guesry Eds. (1981) Elsevier/North Holland Biomedical Press, Amsterdam, New York, Oxford). Finally, the major drawback of the plasma-derived HBsAg 22 nm particle containing vaccine, is its potential health hazard. Although the methods of production employ materials to inactivate possible co-purified contaminants which may include AIDS virus, the potential danger still exists that such vaccines may cause undesirable side-effects (see Walgate, Nature 304: 297 (1983). For this reason the use of recombinant DNA techniques has been applied to the production of 22 nm HBsAg particles for vaccines, which provides for an efficient and safe method of obtaining HBsAg particles free of potentially dangerous human plasma-derived contaminants.

2) Production of HBsAg Vaccines by Recombinant Methods in Procaryotic (*Escherichia coli*) Systems The process for construction of recombinant vectors and plasmids for expression of HBsAg and for purification of HBsAg from prokaryotic systems has been described (for example, see Galilbert et al., U.S. Pat. No. 4,428,941, issued Jan. 31, 1984 and Takeda Chem. Industries patent applications EPO 068719 A2, published Jan. 5, 1983 and WO 86/00640, published Jan. 30, 1986). The methods for producing HBsAg from these transformed bacterial systems are based on those previously described for plasma-derived HBsAg. However, as these prokaryotic systems are incapable of secreting the HBsAg produced, an additional step of lysing transformed cells is necessary. This gives rise to the possibility of copurifying potentially hazardous bacterial endotoxins. Further, prokaryotic systems are neither able to glycosylate HBsAg products nor to assemble them into 22 nm particles. Vaccines produced this way are thus inferior to plasma-derived products (see Charnay et al., Nature 286: 893–895 (1980).

Thus, eucaryotic expression systems for recombinant HBsAg production have been developed; these systems are able to produce HBsAg that is both glycosylated and assembled into 22 nm particles.

3) Production of HBsAg Vaccines in Eucaryotic Cell Culture Employing Yeast Cells Examples of HBsAg vaccines produced in eucaryotic cell culture employing yeast cells include the commercially available RECOMBIVAX HB vaccine, produced by Merck, Sharp and Dohme (MSD) (see Emini et al., J. Infection 13: 3–9 Supplement A (1986)) and the recombinant HBsAg vaccine produced by SmithKline Beckman Corp. (see U.S. Pat. No. 4,649,192, issued Jan. 10, 1987 and EPO Application 199698A, published Oct. 29, 1986).

The HBsAg particles produced by these methods, however, are the products of only the S region having no Pre-S1 or Pre-S2 determinants as the transforming plasmid contains only the S region sequence. These particles are therefore not as immunogenic as the "natural" plasma-derived particles. Yeast cells are also incapable of secreting HBsAg particles, and although they can glycosylate HBsAg proteins, this glycosylation is not the same as that of mammalian cells. Although assembly of 22 nm particles takes place in yeast, the particles are unstable. The method of production requires chemical treatment of the yeast-produced HBsAg to achieve a final product similar to that of plasma origin; also formalin treatment is deemed necessary to make the product safe for human use. Both of these methods as well as purification steps employing detergents and urea can alter the HBsAg molecule structurally which can lead to a loss of antigenicity, and increase the costs of production.

More recently, yeast systems have been employed to produce HBsAg particles which contain Pre-S2 determinants in addition to the S region determinants (see for example EPO 171908 A3, published Feb. 19, 1986, Takeda Chem. Ind. Japan; and EPO 175261 A2, published Mar. 26, 1986, Chiron Corp.). Although these proposed vaccines do contain Pre-S2 region determinants, they still lack those of the Pre-S1 region. Further, the methods of production are still problematic as described above because of the use of the yeast system.

Thus, the system for producing HBsAg particle vaccines that appears to have the most advantages is the mammalian cell culture method.

4) Vaccines and Their Methods of Production in Mammalian Cell Culture Systems

In mammalian cell culture systems glycosylation of the HBsAg particles is the same as that of "natural" HBV particles from human carriers. The HBsAg particles produced are also assembled in the "natural" way requiring no further chemical manipulations. Finally, the 22 nm HBsAg particles are secreted by these cells into the culture medium from which they may be easily purified without lysing the cells.

However, a major problem in the synthesis of recombinant HBsAg vaccine in mammalian tissue culture is the synthesis of the complete spectrum of the HBsAg proteins assembled into authentic 22 nm HBsAg particles. It appears that the Pre-S1 containing proteins (P-39 and GP-42) inhibit the secretion of 22 nm HBsAg particles (see for example Ou and Rutter, J. Virol. 61: 782–786 (1987); Persing et al., J. Virol. 61: 1672–1677 (1987)).

Some potential HBsAg vaccines produced by the mammalian cell system used heterologous oncogenic viral expression vectors (e.g. SV40, adenovirus) to direct the expression of HBsAg. These methods resulted in the production of HBsAg particles which did not contain Pre-S1 determinants, having only Pre-S2 and S regions expressed. The use of heterologous regulatory elements to express the HBsAg particle results in inefficient assembly thus leading to lower yields. Because of the lower yields and lack of pre-SI region, it is also immunogenically inferior. Finally, the purification methods described in these systems are both time-consuming and expensive, commonly involving the use of PEG or ammonium sulphate fractionations followed by ultracentrifugations to achieve purified HBsAg (see for example EPO 0389765 A1, published Oct. 28, 1981, EPO 145589 A3, published Jun. 19, 1985; EPO 201416 A1, published Nov. 12, 1986; and EPO 185573 A1, published Jun. 25, 1986, all assigned to the Pasteur Institute).

Other processes to produce HBsAg particles from recombinant mammalian cell culture have been described (see, for example, EPO 168234 A2, published Jan. 15, 1986, assigned to Genentech Corp.). This system, however, also employs costly time consuming steps of ammonium sulphate or PEG fractionation and centrifugations to achieve a purified product. The final product of HBsAg particles in this system contains only the S region proteins.

Recently, a system was described which claimed success in using a mammalian cell culture system to produce HBsAg particles that contain proteins having all the immunogenic determinants, namely Pre-S1, Pre-S2 and S. However, this system also uses a heterologous regulatory sequence for gene expression (a mouse metallothionein promoter) which requires culture of cells in the presence of heavy metal ions and/or steroid hormones. These may be potentially harmful if they are not removed from the final product. In addition, the method of production described also contains costly and time consuming steps of PEG fractionation and subsequent centrifugation to achieve a purified product. Further, because of the use of heterologous gene regulatory sequences in the expression system, the stoichiometry of Pre-S1, Pre-S2 and S determinants may not be ideal for achieving an HBsAg product that has high immunogenicity. (See EPO 198474 A1, published Oct. 22, 1986, assigned to Endotronics.)

5) Novel Method of Vaccine Production in Mammalian Cell Culture Systems

In view of the above-described drawbacks in the production of recombinant mammalian cell vaccines, applicant has developed a novel, inexpensive process to produce large amounts of highly purified HBsAg particles that are highly immunogenic and bear a close resemblance to the "natural" product. Such particles provide the basis for a very effective and inexpensive vaccine. In addition, the novel product contains all of the antigenic determinants, namely those of the Pre-S1, Pre-S2 and S regions which are produced in an expression system employing the "natural" HBV gene regulatory sequences, resulting in particles being stoichiometrically similar to the "natural" plasma-derived particles.

SUMMARY OF THE INVENTION

The subject invention provides a novel process for producing purified, hepatitis B surface antigen particles which comprises:

(a) culturing mammalian cells which produce the particles in a culture medium so that the cells secrete hepatitis B surface antigen particles into the culture medium, the medium being supplemented with a serum which is free of molecules having a molecular weight greater than about $3 \times 10^5$ daltons;

(b) removing whole cells, cellular debris and particle aggregates from the resulting culture medium containing the hepatitis B surface antigen particles;

(c) treating the resulting culture medium so as to concentrate and purify the hepatitis B surface antigen particles present therein; and (d) recovering the resulting concentrated, purified hepatitis B surface antigen particles.

In an especially preferred process of the invention, a purified, concentrated human hepatitis B surface antigen may be obtained by:

(a) culturing mammalian cells which produce the particles in a culture medium so that the cells secrete human hepatitis B surface antigen particles into the culture medium, the medium being supplemented with a serum which is free of molecules having a molecular weight greater than about $3 \times 10^5$ daltons;

(b) removing whole cells, cellular debris and particle aggregates from the resulting culture medium containing the human hepatitis B surface antigen particles;

(c) treating the resulting culture medium so as to obtain a solution containing concentrated human hepatitis B surface antigen particles;

(d) treating the resulting solution containing concentrated antigen particles so as to decrease the DNA content of the solution;

(e) adjusting the pH of the then-resulting solution containing concentrated and purified surface antigen particles so as to, if necessary, obtain a pH between about 3.0 and about 7.0;

(f) purifying the concentrated surface antigen particles present within the resulting solution; and (g) recovering the purified, concentrated human hepatitis B surface antigen particles.

More specifically, the subject invention concerns a novel process for purifying hepatitis B surface antigen particles, specifically highly immunogenic 22 nm HBsAg particles. These particles are used as an antigen to elicit an immune response to neutralize HBV viral infection against target cells. More particularly, the purification process is characterized in that a novel prefractionation step, i.e., via ultrafiltration, is employed to remove molecules having a molecular weight greater than about $3 \times 10^5$ daltons from a culture media into which the hepatitis B surface antigen particles are secreted.

The purification process of the subject invention involves various steps. In the first step, HBsAg particles were grown and secreted into a culture media supplemented with a growth serum. The culture media was first pre-fractionated to remove cell contaminants having a high molecular weight, i.e., above 300K. Prefractionation of the supplemented culture media is an important step allowing high purity to be obtained employing the least number of purification steps. The molecules having a molecular weight greater than about $3 \times 10^5$ daltons include high molecular weight protein complex contaminants which originate in the fetal calf serum used in the culture media and their prior removal has the following advantages:

(1) cells may be grown in culture media containing high levels of FCS;

(2) cell growth is enhanced because the high molecular weight complexes may possibly be inhibitory to cell growth; and (3) purification of HBsAg is simplified because these high molecular weight protein complexes are usually the major contaminants removed by purification processes.

Subsequent purification steps require primarily separation of high molecular weight HBsAg particles from lower molecular weight molecules, i.e., protein contaminants. First, whole cells, cellular debris and particle aggregates from the resulting culture medium containing the hepatitis B surface antigen particles are removed. The resulting culture medium is then treated so as to concentrate and purify the hepatitis B surface antigen particles present therein, and the resulting concentrated, purified hepatitis B surface antigen particles are then removed. These steps are described in greater detail in the examples which follow, in particular in Example 5, below.

In an especially preferred embodiment of the invention, purified, concentrated human hepatitis B surface antigen is produced. The process comprises, subsequent to the first three steps of the purification process taught in Example 5, i.e., prefractionation of the culture media, removal of whole cells, cellular debris and particle aggregates from collected culture media containing HBsAg particles, and treatment of the resulting culture medium so as to obtain a solution containing concentrated human HBsAg particles, a variation of the purification process described above. The resulting solution containing concentrated antigen particles is treated so as to decrease the DNA content of the solution, and then the pH is adjusted, if necessary, so as to obtain a pH between about 3.0 and about 7.0. In one preferred embodiment of the invention, the pH is adjusted by treatment of the solution with an acid so that turbidity develops. The turbidity contains the protein contaminants and can be separated from the hepatitis B surface antigen particles. The purified, concentrated human hepatitis B surface antigen particles are then recovered. These differences and the advantages of these differences over the process used in Example 5 are described in greater detail in Example 11.

Using the methods of the invention, enhanced levels of cell growth in media containing FCS is achieved, together with the ability to highly purify in a simplified way, HBsAg particles secreted by these cells. The method does not employ polyethylene glycol (PEG) or ammonium sulphate fractionations nor separations by centrifugation (including ultracentrifugation) or affinity chromatography. The method is rapid and efficient resulting in high yields of highly purified product and, because it is based on components that may be recycled, it is very inexpensive. Applicant is thus able to produce a product of high purity at very low cost. This thus provides applicant with the ability to provide an effective HBV vaccine with a much wider spectrum of potential users who could previously not afford the much more expensive presently available vaccines.

Finally, the invention provides a HBsAg particle produced by a mammalian cell system which contains all of the naturally occurring antigenic determinants (Pre-S1, Pre-S2 and S) in amounts that resemble the "natural" stoichiometry. This product is immunogenic for all potential users and can overcome problems of non-responsiveness to S region or Pre-S2 region determinants by having Pre-S1 determinants as well (see, for example, Zuckerman, J. Infection 13: 61–67 (Supplement A) (1986)).

BRIEF DESCRIPTION OF THE FIGURES

FIG. 1: Schematic representation of pSPHBV8-1 construction. p7.5AL26 (11,800 bp) was digested with PstI and the 3800 bp fragment isolated. The fragment, containing HBV sequences, flanked by human Alexander DNA was subcloned in the PstI site of pSP64 by ligation with $R_4$ DNA ligase.

FIG. 2: Schematic representation of pSPHBVB8 construction. pSPHBV8-1 was fully digested with EcoRI and XbaI, followed by isolation of the 500 bp fragment containing HBV-AL26 promoter and coding sequence for Pre-S1. In a separate reaction, pSPHBV8-1 was digested with EcoRI and PstI and the 2400 bp fragment, containing coding sequences for Pre-S2 and S, as well as HBV-AL26 enhancer and polyadenylation signal, was isolated. Both fragments were subcloned in tandem into pSP65 cut with XbaI and PstI, in a triple-ligation procedure.

FIG. 4: FIG. 4 is a flow diagram illustrating preferred method A for production and purification of HBsAg particles.

(a) known standards (Abbott) were compared to a calibration curve of applicant's recombinant HBsAg (CHO).

(b) calibration curve of recombinant HBsAg vaccine produced in CHO cells—applicant's vaccine (CHO) was compared to calibration curves of plasma derived (HBsAg) vaccine—HEPTAVAX B ® and with yeast recombinant vaccine—RECOMBIVAX HB.

Figure 7:
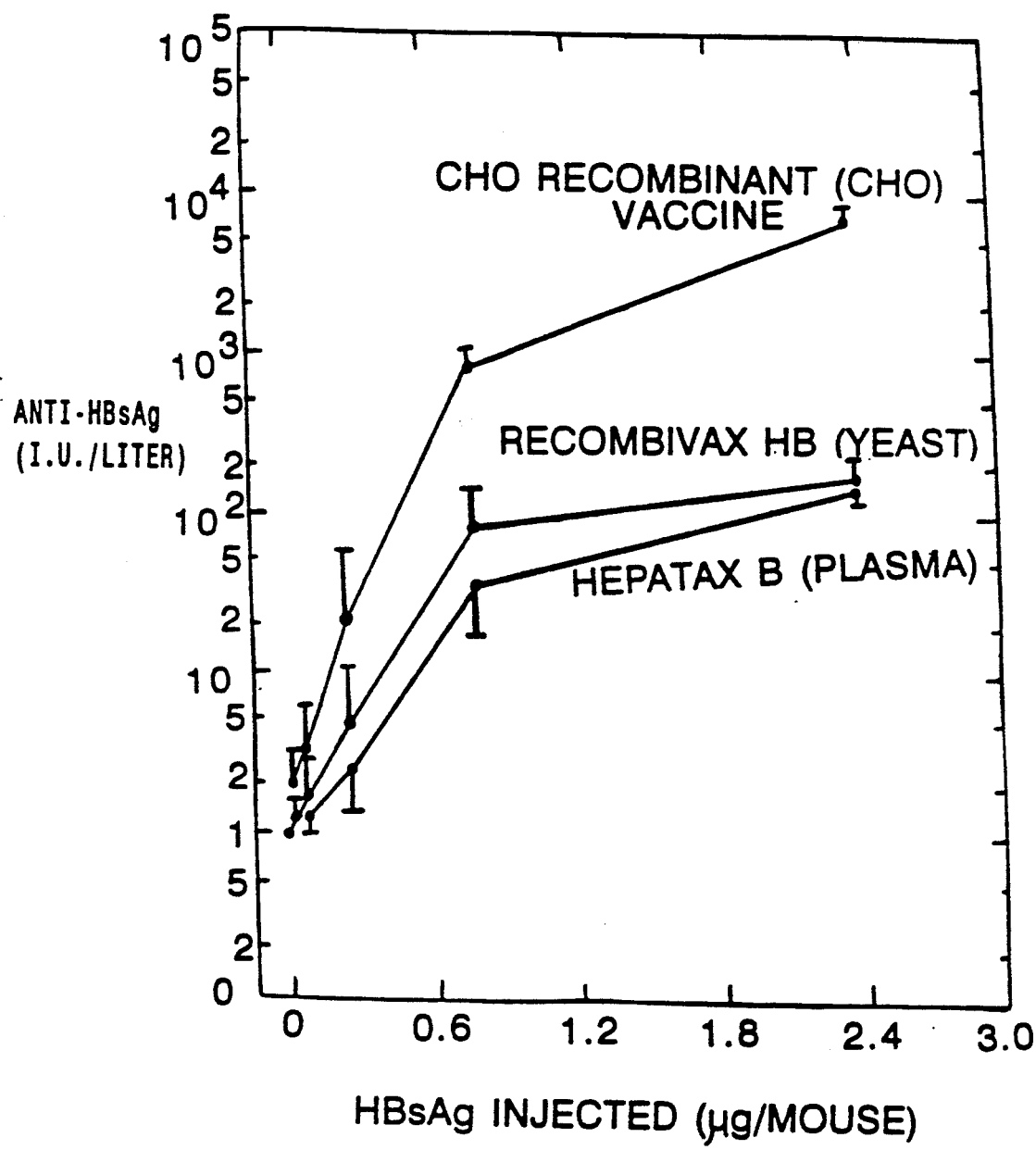

FIG. 7: HBsAg potency assay by seroconversion: applicant's vaccine (CHO) was compared with plasma derived vaccine—HEPTAVAX B ® and with yeast recombinant vaccine—RECOMBIVAX HB.

Balb/c mice were infected intraperitoneally with 1 ml vaccine (10 mice were used for each vaccine concentration). Thirty days after injection the mice were exsanguinated and serum was tested for presence of anti-HBsAg antibodies by AUSAB EIA kit (ABBOTT) calibrated against reference serum (WHO).

FIG. 8: This is a flow diagram, illustrating the especially preferred method for production and purification of HBsAg particles (preferred method B).

FIG. 9: This is a flow diagram illustrating preferred method C for production and purification of HBsAg particles.

Figure 10:
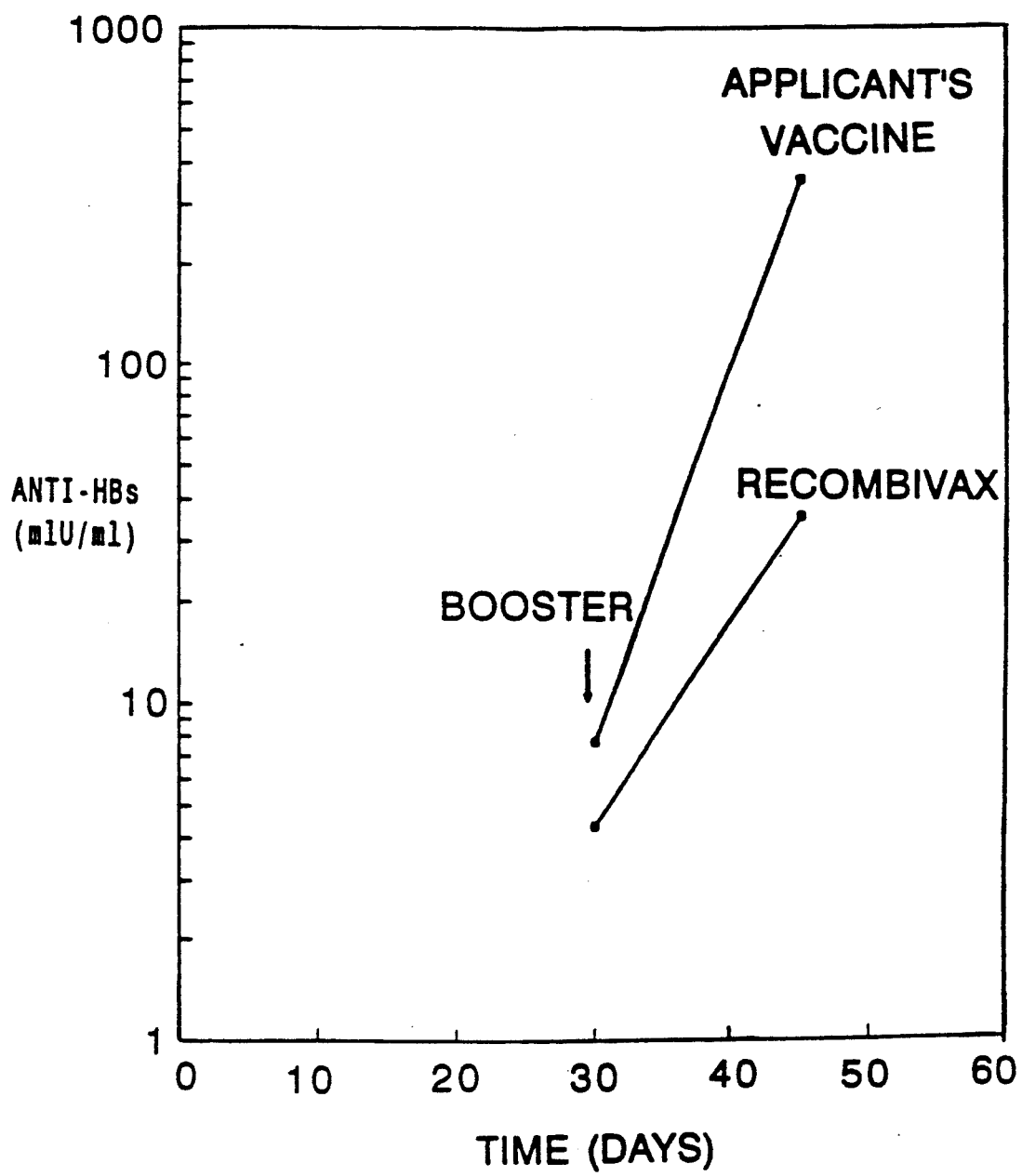

FIG. 10: Detection and quantitation of anti-S antibodies in non-responding mice injected with applicant's vaccine compared with a yeast recombinant vaccine—RECOMBIVAX HB.

DETAILED DESCRIPTION OF THE INVENTION

The subject invention provides a novel process for producing purified, hepatitis B surface antigen particles which comprises:

(a) culturing mammalian cells which produce the particles in a culture medium so that the cells secrete hepatitis B surface antigen particles into the culture medium, the medium being supplemented with a serum which is free of molecules having a molecular weight greater than about $3 \times 10^5$ daltons;

(b) removing whole cells, cellular debris and particle aggregates from the resulting culture medium containing the hepatitis B surface antigen particles;

(c) treating the resulting culture medium so as to concentrate and purify the hepatitis B surface antigen particles present therein; and (d) recovering the resulting concentrated, purified hepatitis B surface antigen particles.

The particles produced by the above process may be human hepatitis B surface antigen particles.

The invention further provides a process for recovering purified HBsAg particles comprising further purifying the HBsAg particles obtained in step (c) to remove low molecular weight contaminants by subjecting a solution containing the particles through a chromatography column and recovering these particles. Concentration of step (c) is conducted under suitable conditions to allow further purification of the particles in a non-batch purification system.

It is an important element of the invention that the serum which is added to the medium containing the mammalian cells which secrete the hepatitis particles, such as fetal calf serum, be free of high molecular weight contaminant proteins (i.e., proteins having a molecular weight greater than about 300,000 daltons) prior to placing the cells in the medium. Such proteins are removed from the serum by, for example, pre-fractionating the serum, i.e., through ultrafiltration.

Failure to remove contaminating proteins having a molecular weight greater than about 300K from the serum results in high levels of contaminating proteins in subsequent purification steps, lower yields and reduced purity.

While prefractionation was effected in the subject invention by using an ultrafiltration step, it will be appreciated by those skilled in the art that any method for reducing high molecular weight contaminant proteins from the serum added to the medium will provide the same results.

Separation of the hepatitis B surface antigen particles from whole cells, cellular debris and particle aggregates may also be effected by any means known to those skilled in the art although an ultrafiltration step is preferred. The filtrate containing the HBsAg particles obtained from the ultrafiltration step is then collected for further purification.

Because the batch volumes used in separation step (b) are too large to be applied to the preferred subsequent purification steps on chromatographic columns, e.g., gel chromatography steps, the HBsAg particles may be further concentrated and further purified. Purification is preferably accomplished by subjecting the filtrate obtained after separation step (b) to an ultrafiltration step which removes contaminating molecules having molecular weight below about 300K. The retentate containing the desired HBsAg particles may then be further purified. In a preferred embodiment of the invention, further purification is effected by dialysis and dialysis is followed preferably by another ultrafiltration step to further concentrate.

The concentrated, purified HBsAg particles may then be further purified by using chromatography, preferably a gel filtration column, to further remove contaminating small molecular weight particles. The gel filtration step is preferably repeated a second time for further purification. The gel filtration chromatography is preferably done on a column of an allyl dextran covalently cross-linked with N,N' methylene bisacrylamide. The gel filtration column excludes molecules of molecular weight greater than about $1 \times 10^6$ daltons. The process is described in greater detail in the examples which follow, particularly Example 5.

In an especially preferred process of the invention, a purified, concentrated human hepatitis B surface antigen may be obtained by:

(a) culturing mammalian cells which produce the particles in a culture medium so that the cells secrete human hepatitis B surface antigen particles into the culture medium, the medium being supplemented with a serum which is free of molecules having a molecular weight greater than about $3 \times 10^5$ daltons;

(b) removing whole cells, cellular debris and particle aggregates from the resulting culture medium containing the human hepatitis B surface antigen particles;

(c) treating the resulting culture medium so as to obtain a solution containing concentrated human hepatitis B surface antigen particles;

(d) treating the resulting solution containing concentrated antigen particles so as to decrease the DNA content of the solution;

(e) adjusting the pH of the then-resulting solution containing concentrated and purified surface antigen particles so as to, if necessary, obtain a pH between about 3.0 and about 7.0;

(f) purifying the concentrated surface antigen particles present within the resulting solution; and (g) recovering the purified, concentrated human hepatitis B surface antigen particles.

This especially preferred example is described further in Example 11. According to this especially preferred method, the solution containing concentrated antigen particles recovered from step (c) is further purified prior to recovery. Steps a, b, and c of the especially preferred method are the same as in the process described in Example 5, and the above description of the process of Example 5 also applies to the process of Example 11. An additional preferred method is described in Example 13.

After the culture medium is treated so as to obtain a solution containing concentrated human hepatitis B surface antigen particles, the resulting solution is treated so as to decrease the DNA content of the solution. In one preferred method (see Example 11), the treatment to decrease the DNA content comprises adding DNase to the solution. In another preferred method (see Example 13), the treatment to decrease the DNA content comprises subjecting the solution to anion exchange chromatography, preferably on a column of crosslinked agarose having diethylaminoethyl functional groups present thereon. This anion exchange chromatography step may also follow the treatment with a DNase solution.

The pH of the then-resulting solution containing concentrated and purified surface antigen particles is then adjusted, if necessary to obtain a pH between about 3.0 and about 7.0. In one preferred embodiment of the invention, the pH is adjusted by treating the then-resulting solution with an acid; and turbidity develops. The turbidity contains protein contaminants and can be separated from the human hepatitis B surface antigen particles, preferably by centrifugation. This step is the further purification of the acid-treated antigen particles.

Alternatively, DNA and protein contaminants may be removed from the above solution of antigen particles by using ion exchange chromatography, preferably anion exchange chromatography, whereby the HBsAg particles elute with the flow-through volume and DNA and protein contaminants are bound to or retarded by the column. The anion exchange column is preferably a DEAE anion exchange column. In an especially preferred embodiment of the invention, the anion exchange column used to remove the DNA and other contaminants is a crosslinked agarose column with DEAE functional groups. One example of such a column is DEAE-Sepharose. This process is described in greater detail in Example 13.

Another alternative is to combine the above two procedures, i.e., to decrease the DNA content by DNase treatment followed by acidification and subsequent removal of DNA on a DEAE column.

While it will be clear to those skilled in the art that any purification method may be used for further purification after removal of DNA, e.g., cation or anion exchange chromatography, strong cation exchange chromatography is preferred, such as using a column with a sulfonic acid functional group. In an especially preferred embodiment of the invention, the cation exchange column used for further purification is a copolymer of N-acrylolyl-2-amino-2-hydroxymethyl-1.3 propane-diol which has as sulfonic acid functional group the chemical grouping:

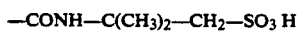

—CONH—C(CH$_3$)$_2$—CH$_2$—SO$_3$H

One example of such a column is SP-TRISACRYL LS.

The highly purified, concentrated antigen particles may also be treated with formaldehyde to inactivate any live organisms and viruses present, prior to further concentration, preferably by ultrafiltration. The resulting further concentrated particles are then purified by chromatography, preferably gel filtration chromatography. A preferred gel filtration column is of an allyl dextran covalently crosslinked with N,N' methylene bisacrylamide.

As described in Example 10, when alternate steps to the preferred steps of the invention were used, many problems arose. Thus, for example, when centrifugation was used for separation rather than ultrafiltration, major cell contaminants such as cell membranes and lipid complexes were not removed leading to reduced overall yield and decreased HBsAg particles purity. The centrifugation is also costly and time-consuming. Using a 0.22 micron membrane sterilization system resulted in different problems described in the examples.

Similarly, when PEG was used to concentrate rather than ultrafiltration, only 75% recovery of HBsAg particles was found. Also, purity was lower and the process was more time-consuming.

Accordingly, although alternative methods such as those described in Example 10 and those which would be appreciated by a person skilled in the art may be used, preferred method steps are discussed in Example 5. Moreover, as discussed above, an especially preferred embodiment of the invention is detailed by Example 11.

Any mammalian cell capable of expressing cDNA encoding hepatitis B surface antigen may be used. Preferred cells are the Chinese Hamster Ovary (CHO) cells, especially CHO-HB200 cells.

Hepatitis B surface antigen is obtained by culturing the mammalian cell, e.g., CHO-HB200. Culture conditions are known to those skilled in the art. Culturing may be performed in roller bottles or in fermentors using microcarriers.

Purified hepatitis B surface antigen particles are recovered from the processes. As described above, these purified particles comprise the pre-SI, pre-S2 and S surface antigen polypeptides of hepatitis B surface antigen and the purity level obtained may reach as high as 95 to 98-99% purity (95% to 98-99% free of protein contaminants). The purified, hepatitis B surface antigen particles further comprise pre-S1, pre-S2 and S surface antigen polypeptides in stoichiometric amounts approximating those of plasma-derived particles.

More specifically, purified hepatitis B surface antigen particles may contain surface antigen polypeptides wherein the S surface antigen polypeptide comprises 75-80% of the particle, the pre-S2 surface antigen polypeptide comprises 10-15% of the particle and the pre-S1 surface antigen polypeptide comprises 5-10% of the particle. In one specific embodiment of the invention, the S surface antigen polypeptide comprises 78% of the particle, the pre-S2 surface antigen polypeptide comprises 14% of the particle and the pre-S1 surface antigen polypeptide comprises 8% of the particle.

In a more specific embodiment of the invention, the invention comprises purified hepatitis B surface antigen particles wherein the surface antigen polypeptides may be found in the following amounts:

| S | 24 kD non-glycosylated | 62.4% |
|---|---|---|
| S | 27 kD glycosylated | 15.6% |
| Pre-S2 | 33 kD singly glycosylated | 10.8% |
| Pre-S2 | 36 kD doubly glycosylated | 3.2% |
| Pre-S1 | 39 kD non-glycosylated | 6.1% |
| Pre-S1 | 41 kD glycosylated | 1.9% |

It will be understood by those skilled in the art that the amounts discussed in the preceding paragraphs may vary depending on the purity of the recovered product.

The invention also provides a hepatitis B surface antigen vaccine comprising an effective immunizing amount of the hepatitis B surface antigen particles produced by the process described above, and a suitable carrier.

EXAMPLES

The examples which follow are set forth to aid in understanding the invention but are not intended to and should not be construed to, limit its scope in any way. The examples do not include detailed descriptions for conventional methods employed in the construction of vectors, the insertion of genes encoding polypeptides into such vectors or the introduction of the resulting plasmids into hosts. The examples also do not include detailed descriptions for conventional methods employed for assaying the polypeptides produced by such host vector systems. Further, the examples do not include detailed descriptions for conventional methods of mammalian tissue culture nor recombinant DNA transformation of the tissue culture cells. Finally, the examples do not include detailed descriptions for conventional methods of ultrafiltration and gel filtration, to purify polypeptides produced by the transformed tissue culture cells.

Such methods are well-known to those of ordinary skill in the art and are described in numerous publications, for example the following:

General Molecular Biology Methods

Maniatis et al., Molecular Cloning: A Laboratory Manual, Cold Spring Harbour Laboratory, N.Y. (1982); Davis et al., Basic Methods in Molecular Biology, Elsevier, N.Y., Amsterdam (1986).

Mammalian Tissue Culture Methods

Uslaub and Chasin, Proc. Natl. Acad. Sci. 77: 4216-4220 (1980); Pellicer et al., Science 209: 1414-1422 (1980); Laub et al., J. Virol. 48: 271-280 (1983); petzer et al. in Viral Hepatitis and Liver Disease, Vyas et al. (eds), pp. 477-485, Grune and Stratton Inc., Orlando, Fla. (1984); Michel et al., Bio/Technology 3: 561-566 (1985).

Ultrafiltration Methods

Trudel et al., Process Biochem. 18: 2-9 (1983).

Gel Filtration Methods

Fischer in "Gel Filtration Chromatography", Elsevier, Amsterdam (1980).

Mammalian Cell Lines

Applicant has used cell lines designated CHO$^{200Mr}$ p7.5AL26 and CHO$^{50Mr}$ p 7.5AL26 developed at the Weizmann Institute/Yeda Research and Development Company and deposited with the Institute Pasteur under Deposition Nos. I-574 and I-575, respectively. The construction of these plasmids is described in pending European patent applications. Other mammalian cell lines similarly containing the HBsAg gene region on a selectable transforming plasmid may also be employed in performing the invention.

EXAMPLE 1

Cell Lines and Plasmids Developed and Employed in this Invention

Applicant used CHO cell line CHO$^{Mr200}$ p7.5AL26 (FIG. 1) to produce and purify HBsAg particles. However, applicant found this cell line to be contaminated with mycoplasmas, which therefore necessitated curing before use.

This cell line was constructed by transfecting CHO dhfr cells with DNA from plasmid p7.5AL26 and DNA from a plasmid containing the dhfr gene. The ratio of p7.5AL26 DNA to plasmid DNA containing the dhfr gene was 10:1.

Plasmid p7.5AL26 was constructed by inserting into the EcoRI site of pBR322, a 7.5 Kb EcoRI fragment which contains the entire integrated HBV surface antigen gene including the pre-S1 and pre-S2 regions as well as the HBV promoters designated "TATA" promoter and "SV 40-like" promoter. Moreover, it contains the HBV enhancer element and 2-3 polyadenylation sites downstream from the 3' end. The DNA was isolated by Shaul et al., J. Virol. 51: 776–787 (1984) from Alexander cells and contains flanking host sequences (from Alexander cells) at the 5' and 3' end of the HBV DNA. The transformed cells were then treated with methotrexate (200 nM) and resistant cells were selected.

Other cell lines were transformed With the same HBV DNA which had been treated to remove most or all of the flanking host cell (Alexander) DNA sequences. Thus, for example, a 3.8 Kb Pst DNA fragment from p7.5 AL26 was introduced into pSP64. The resulting plasmid, pSPHBV8-1 contains 100 bp of human DNA upstream of the HBV promoter TATA box and 600 bp of human DNA beyond the P$_J$ region, downstream of the 3' end of the gene.

A. Curing of Cell Line CHO$^{200Mr}$p7.5AL26

Cell line CHO$^{200Mr}$ p7.5AL26 contaminated with mycoplasmas was cured using an antibiotic kit: "BM-CYCLINE" (Boehringer, Mannheim). This kit consists of an antibiotic combination of a pleuromutilin derivative and a tetracycline derivative and is used for the elimination of mycoplasmas from infected cell cultures. The curing was performed exactly according to the protocol supplied with the kit (Boehringer Mannheim catalogue No. 799050 and used herein as reference). Curing was successful resulting in a cell line, which we designate CHO-HB200, that is free of mycoplasmas and produces HBsAg particles at high levels.

B. Production Levels of HBsAg by the Cured CHO$^{Mr200}$ 7.5AL26 Cell Line—CHO-HB200

The constitutive expression of immunoreactive HBsAg by this cell line was initially determined by assaying the medium of confluent cultures. Using the TRAVENOL solid phase radioimmunoassay kit for detection of HBsAg it was determined that the medium of confluent CHO-HB200 cultures contained 3–5 mg/L immunoreactive HBsAg.

C. Stability of Cured CH$^{Mr200}$ 7.5AL26 clone—CHO-HB200

The selected clone CHO-HB200 stably produced HBsAg for at least 6 months.

D. Development of New HBsAg Expression Plasmids

Plasmid pSPHBV8-1 (FIG. 1) was further manipulated, to delete remaining upstream Alexander cell DNA sequences. This was done by subcloning the 500 bp XbaI-EcoRI fragment and the 2400 bp EcoRI-PstI fragment of pSPHBV8-1 into pSP65, yielding pSPHBVB8 (FIG. 2).

Figure 3:
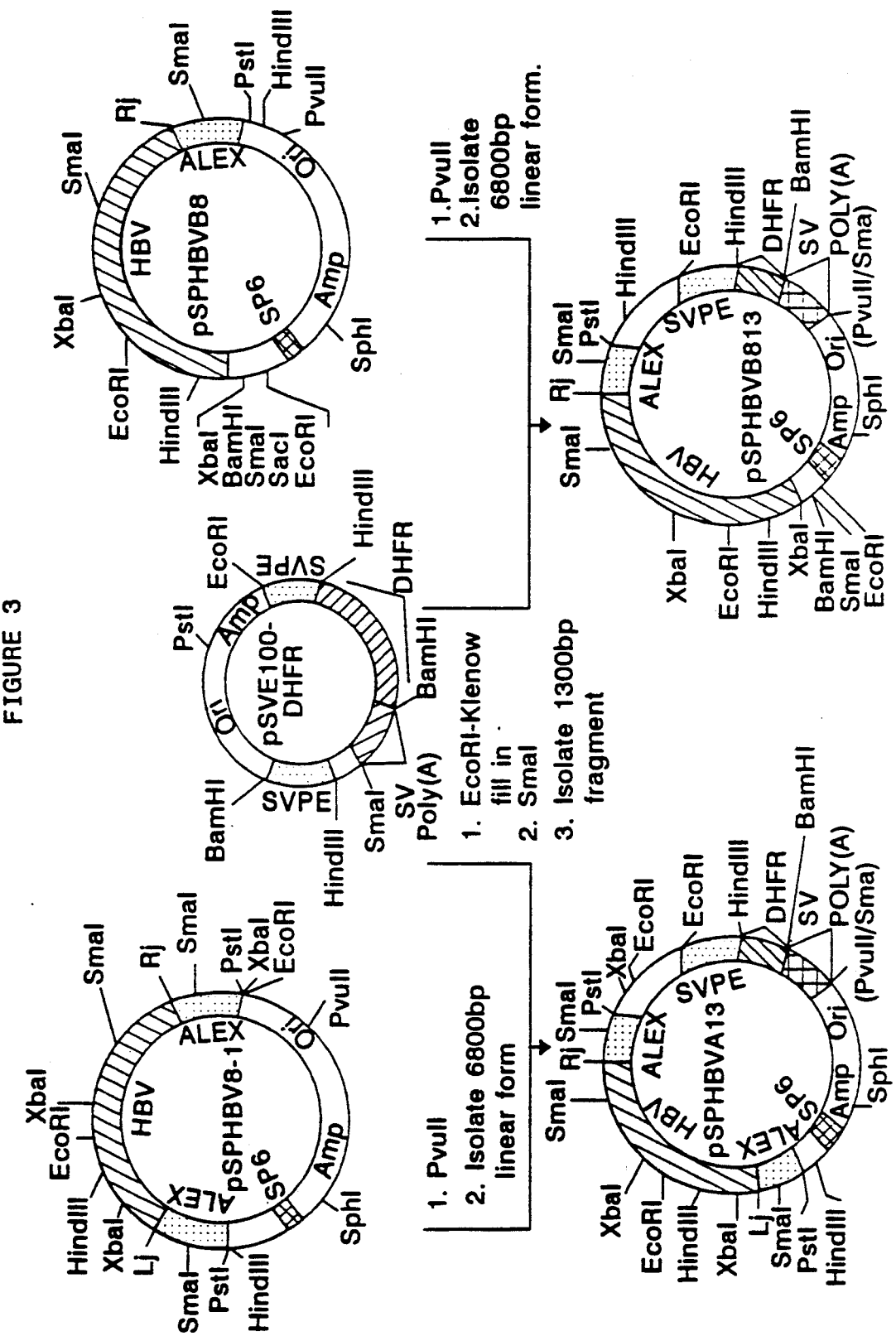
FIG. 3: Schematic representation of pSPHBVA13 and pSPHBVB813 construction. The dhfr gene flanked by SV40 $P_E$ and SV40 poly-adenylation signal was isolated from pSVE100-dhfr by digestion with EcoRI, filling ends in with Klenow fragments and further digestion with SmaI. The 1300 bp blunt-ended fragment was sub-cloned into the PvuII site of pSPHBV8-1 and pSPHBVB8, yielding plasmids pSPHBVA13 and pSPHBVB813 Which harbor sequences for HBsAg as well as dhfr.

The dhfr gene, under control of SV40 early promoter and SV40 polyadenylation site was subcloned into pSPHBV8-1 and pSPHBVB8 yielding pSPHBVAL3 and pSPHBVB813, respectively (FIG. 3). This was performed by subcloning the 1300 bp filled-in EcoRI-SmaI fragment of pSVE100-dhfr, containing the dhfr gene with all regulatory sequences, into the PvuII site of the appropriate HBV plasmid.

The shortened constructs, containing HBsAg gene under control of its natural promoter, as well as the dhfr gene under control of the SV40 early promoter, were transfected into dhfr CHO cells.

EXAMPLE 2

Tissue Culture Methods

The following methods which applicant employed in this invention are generally standard procedures used in tissue culture of mammalian cells. Variations to these methods have been described and may also be employed for the same purposes (for examples of the various methods, including ours, see the following references: Uslaub and Chasin, Proc. Natl. Acad. Sci. 77: 4216–4220 (1980); Pellicer et al., Science 209: 1414–1422 (1980); Laub et al., J. Virol. 48: 271–280 (1983); Petzer et al., in "Viral Hepatitis and Liver Disease", Vyas et al. (eds), pp. 477–485, Grune and Stratton Inc., Orlando, Fla. (1984); and Michel et al., Bio-Technology 3: 561–566 (1985).

A1. Trypsinization

Confluent cultures are trypsinized before being subcultured or preserved in frozen storage. The culture medium, Dulbecco's Modified minimal Eagle's (DMEM.) is discarded from the culture vessel and cold trypsin solution (0.25% diluted 1:3) in PBS is added. (The volume of added trypsin is about 1/10 of the volume of the original growth media). The anchored cells are quickly washed and excess trypsin is removed. After 5–10 minutes at 37° C. during which the residual trypsin is in contact with the cells, growth media (DMEM) supplemented with 5–10% fetal calf serum (FCS) was added to the culture vessel to stop trypsinization. By gentle shaking the anchored cells are dislodged from the walls and suspended in media. These cells are either subcultured or frozen for long-term storage.

Preparation of Trypsin Solution 0.25% (Stock)

The Trypsin solution contains:

| | |
|---|---|
| 80 gr | NaCl |
| 4 gr | KCl |
| 10 gr | dextrose |
| 3.5 gr | NaHCO$_3$ |
| 25 gr | Trypsin (1:300 ICN) |

All the above ingredients are dissolved in 10 liters water, and pH adjusted to 8.5

The above solution is then filtered through a 0.22 micron filter and is frozen (−20° C.) and can be stored for years.

A2. Preparation of Working Trypsin Solution (Dilution 1:3)

Dilute the stock solution 1:3 with a solution containing the same formulation as stock solution (above) but without trypsin.

B. Long-Term Storage of Cells

Whenever long-term storage of cells was needed the following procedure was carried out: confluent cultures were trypsinized as described in Section 1. The suspended cells were washed once or twice in DMEM media supplemented with 10% FCS. After washing, the cells were resuspended in media containing 20% FCS+10% DMSO, to reach a final cell concentration of $3-4 \times 10^6$ cells/ml The vials were left up to 1 hour at room temperature, then transferred to a −20° C. freezer. The following morning the frozen vials were brought to −70° C. for an additional 24 hours. Finally, the vials were placed in liquid nitrogen for long-term storage.

About a week later, 1-3 vials were defrosted for cell viability estimation.

Master and working cell banks were established, in this fashion.

C. Defrosting of Stored Cells

The vial containing the stored frozen cells was quickly removed from the liquid nitrogen storage tank and placed in a 37° C. water bath. The cells were quickly thawed and were transferred to a T flask (75-150 cm$^2$) containing 25-50 ml DMEM supplemented with 10% FCS. After several hours most of the cells were seen to attach to the bottom. Medium was replenished 4 hours after defrosting the cells. After about 5-8 days the culture reached confluence.

EXAMPLE 3

The Roller Bottle System for Cell Culture

A. Growth Media

All CHO cell lines were grown in Dulbecco's modified Eagle's medium (DMEM) containing 10 mM glutamine (Gibco), 20 mM Hepes (Raught Ltd.), 30 mM NaHCO$_3$ (Merck), 150 µg/ml Proline (Sigma) and 40 µg/ml Gentamicin (Sigma). The medium was supplemented with 2-10% Fetal Calf Serum (FCS) (Bocknek), to meet the culture needs. The optimal working pH of the media was in range of 7.15-7.25.

B. Inoculation and Culture Maintenance

Plastic roller bottles 850 cm$^2$ or 490 cm$^2$ (Corning) were used for growing the cells and for HBsAg production. Confluent cultures were trypsinized and the cells were suspended in DMEM media, supplemented with i0% FCS, and used for re-culturing. Each roller bottle was inoculated with 50-100 ml media, supplemented with 10% FCS, containing at least $5 \times 10^6$ cells. The size of inoculum determines the length of time needed for the culture to reach confluency again (it can range between 2-10 days). Several hours after inoculation most of the cells were attached and started to spread. After 24 hours cell divisions could be observed.

It is recommended to use media supplemented with 10% FCS up to the point where culture reaches confluency; at which stage FCS level is then reduced to 2-5%. The reduced FCS level is optimal for a long period of cell maintenance and production. Such cultures could be maintained for 6 months without losing their capacity to produce HBsAg.

The number of cells in confluent cultures varied between $2.10^8-10^9$ cells per roller bottle.

The vigorous metabolism typical of CHO cells, together with the high cell density, caused a rapid pH drop of the medium. This was probably followed by medium depletion on the one hand and by the release of unwanted toxic metabolites, on the other hand. In order to prevent potential damage to the cells, it is recommended to replenish daily the media in confluent cultures.

EXAMPLE 4

Production of HBsAg in Roller Bottle System

The constitutive production of HBsAg by the CHO-HB200 (Example 1) cells was employed for continuous long-term HBsAg production. The production of HBsAg in confluent cultures, with daily single medium replenishment, was stable for at least 6 months. The rate of production was 4-5 mg HBsAg/L/24 h, which was unvaried during this six-month period of continuous culture.

Although large amounts of HBsAg can be produced in roller bottle culturing systems, this method is only suitable for limited commercial production. The major limitations are the amount of labor involved and the inefficient handling.

Therefore, roller bottle systems are recommended for growing cells used to inoculate large-scale production systems, such as spinners and fermentors employing microcarriers.

EXAMPLE 5

Preferred Method A for Production and Purification of HBsAg Particles

As indicated by the title of the Example, the method disclosed in the following Example is one preferred method only. A more preferred method is set forth as Example 11 which is an especially preferred method of the invention. FIGS. 4 and 8 respectively illustrate the flow diagrams for the two methods.

A. Summary of Process

The roller bottles system was employed for production of HBsAg (as described in Examples 3, 4). The medium used contained between 2-10% FCS, preferably 2% FCS, which had been pre-fractionated by ultrafiltration using a PELLICON system (PELLICON tangential flow ultrafiltration "MILLIPORE) with a 300,000 MW cut-off membrane to remove high molecular weight contaminant proteins (Step 1).

Culture media were collected daily and pooled (harvesting). The harvested medium containing HBsAg particles were clarified by PELLICON tangential flow ultrafiltration "MILLIPORE") with a 0.22 micron membrane to remove cells and large cell debris (Step 2). Finally, the clarified crude medium was concentrated and dialyzed (with PBS) by PELLICON tangential flow ultrafiltration ("MILLIPORE") with a 300,000 MW cut-off membrane (Step 3). The concentrate was further purified by two consecutive gel filtration chromatography runs on a SEPHACRYL S-400 column (2.6 cm × 190 cm) (PHARMACIA). After each run the peak fractions containing HBsAg particles were concentrated using a "MINITAN" tangential flow ultrafiltration system ("MILLIPORE") with a 300,000 MW cut-off membrane The purification procedure is summarized in FIG. 4. The results using this novel procedure in purifying HBsAg particles are illustrated in Example 6, which describes production of a 100 mg batch of highly purified HBsAg particles.

The methods employed in the "PELLICON" and "MINITAN" tangential flow ultrafiltration steps are as described in the protocol provided by the manufacturer, (Millipore Corp.). Gel filtration methods using the SEPHACRYL S-400 column, which has a 1 liter bed volume, are as described by the manufacturer (Pharmacia Fine Chemicals). Throughout the purification process applicant employed only phosphate buffered saline (PBS) as the buffer for: ultrafiltrations, dialysis, and gel-filtration chromatography (loading and eluting). Applicant used a calcium ($Ca^{++}$) and Magnesium ($Mg^{++}$)—free PBS Buffer.

B. PBS Buffer, $Ca^{++}$ and $Mg^{++}$-free

The $Ca^{++}$, $Mg^{++}$-free PBS Buffer (×1) is made the following way:

| 8 gr | NaCl |
| 0.2 gr | KCl |
| 1.15 gr | $Na_2HPO_4$ |
| 0.2 gr | $KH_2PO_4$ |

Above constituents are dissolved in 1 liter of $H_2O$ (double distilled—pyrogen free). The pH of the solution is adjusted to 7.25.

C. Detailed Description of the Novel HBsAg Production—Purification Process

Step 1: Prefractionation of Cell Culture Media

CHO-HB200 cells which produce, and secrete into the culture media, HBsAg particles (described in Example i) were grown in the Roller Bottle culture system (described in Examples 3 and 4). Applicant typically grew cells in 20 such roller bottles.

Culture media was supplemented with FCS in the following way: to inoculate roller bottles culture media supplemented with 10% FCS was used. To replenish cell culture media on a daily basis (by replacing day-old media with fresh media) culture media supplemented with 2-5% FCS, preferably 2% FCS, was used. In both above cases, the culture media supplemented with FCS was first pre-fractionated using the Pellicon ® Tangential Flow Ultrafiltration System with a 300,000 MW cut-off membrane. The pressure on the inlet and outlet gauges was typically in the 0 psi range. Only the filtrate (FCS-supplemented media components below 300,000 MW) is added to the cells.

To inoculate the roller bottles, 100 ml of pre-fractionated 10% FCS-supplemented media containing at least $5 \times 10^6$ CHO-HB200 cells was poured into each roller bottle. The cells were grown in this medium until they reached confluency (between 2-10 days).

When cells reached confluency, $2 \times 10^8$–$1 \times 10^9$ cells per roller bottle, purification of HBsAg particles produced by the cells was initiated. The 10% FCS-supplemented inoculating media was removed from the cell cultures and discarded. This was replaced with the pre-fractionated 2% FCS-supplemented media. Cells were grown in this media for at least 6 months, with daily changes of media. The confluent cells produce 4-5 mg HBsAg particles per liter (10 roller bottles) per day. The culture media is removed from the roller bottles daily ($20 \times 100$ ml = 2 liters per day) and contains the secreted HBsAg particles. These collected media are pooled and stored at 4° C. When 25 liters of daily collected o and pooled confluent culture media are accumulated (80-100 mg HBsAg, 13 days culture), batch-wise purification of HBsAg particles from this pooled media begins as described in Step 2.

The unique step of prefractionation of FCS-supplemented culture media described above enables applicant to achieve purification of HBsAg particles to a high degree of purity employing the least number of purification steps. The reasons for this may be summarized as follows.

The major contaminants in culture media containing secreted HBsAg particles are proteins originating in the FCS. To achieve best culture conditions FCS is necessary and thus cannot be eliminated from cell culture. The secreted HBsAg particles have a high molecular weight and therefore the proteins contaminating the HBsAg fraction during purification will be those of high molecular weight. Using the prefractionation step described above with a 300,000 cut-off membrane, applicant removes most of the high molecular weight protein contaminants from the culture media. Applicant is, in effect, adding to the culture only FCS-supplemented media components that have molecular weights below 300,000 MW. Applicant has thus excluded high molecular weight protein complexes, such as antibody complexes and polyalbumin aggregates, from the cell culture. In fact, comparing the growth and HBsAg production characteristics of cells grown in pre-fractionated media to those grown in equivalent non-pre-fractionated media, applicant observed that the former media was superior in both respects. Thus, pre-fractionated media provide 2 major advantages: better cell growth and reduced contaminant levels in HBsAg purification.

Finally, the subsequent purification steps require mainly the separation of high molecular weight HBsAg particles from the lower molecular weight protein contaminants. These contaminants include, as a major fraction, the FCS-derived albumin whose molecular weight is about 97,000 daltons.

Step 2: Clarification of Collected Culture Media Containing HBsAg Particles

This is actually the first step of the HBsAg purification process, whereby dissociated whole cells and cell debris present in the collected media (containing HBsAg) are removed from the media. This is usually referred to as clarification of the crude culture media. Applicant employs a PELLICON tangential flow ultrafiltration with a 0.22 micron filter to clarify the HBsAg-containing culture media. Typically a 25 liter batch (80-100 mg HBsAg particles) is filtered in this system per run. The pressure readings on the inlet and outlet gauges are kept to 0 psi. Larger batches or an increased number of batches may be processed in this system as it is capable of filtering several hundred liters of media per hour. After each batch is filtered the system is washed with 5-10 L of PBS. This is therefore a very rapid process and industrially applicable.

Only whole cells and large cell debris (>220 nm) aggregates (e.g. membranes and membrane complexes, large cellular organelles) are retained by the 0.22 micron filter (220 nm). Only the filtrate (containing the 22 nm HBsAg particles) of this clarification ultrafiltration step is collected and further purified according to steps 3-5. The volume of the filtrate is the same as the starting volume, namely 25 liters per batch. No losses (100% recovery) in HBsAg particle or total culture media protein are incurred by this clarification ultrafiltration step.

Step 3 Concentration and Purification of HBsAg Particles from the Clarified Culture Medium The volume of the clarified crude culture media (step 2) is liters per batch. To purify specifically the HBsAg particles from this culture media requires a concentration step first. Batch volumes as large as applicant's cannot be applied directly to the purifying gel filtration columns used in the final steps of the purification process (steps 4, 5). Thus a concentration step is necessary, and a concentration step that also specifically purifies HBsAg particles from the rest of the culture media constituents is desired. Such a step was achieved by concentrating the clarified crude culture media in a "PELLICON" tangential flow ultrafiltration system with a 300,000 MW cut-off membrane. This system also enabled applicant to dialyze, within the closed ultrafiltration system, the HBsAg particles which are retained by the 300,000 MW membrane.

Applicant adds 25 L of clarified crude media to the Pellicon ® 300,000 MW filter system (above) and discards the filtrate (molecules which include albumin of molecular weight below 300,000). The retentate (molecules which include HBsAg particles above 300,000 MW) on the filter is dialyzed against 10 L of PBS (10×1 L). After dialysis the volume of retentate was 660 ml, which constitutes an approximately 40-fold concentration.

The 600 ml concentrate (or retentate) is then collected and further concentrated in a "MINITAN" tangential flow ultrafilration system with a 300,000 MW cut-off membrane. The MINITAN system is more suited to small volumes (up to 1 liter) than the "PELLICON system". The filtrate of the MINITAN ultrafiltration is discarded and only the retentate is collected. Typically, approximately 150 mls of retentate (or concentrate) are recovered from the Minitan ® System when approximately 660 ml of PELLICON concentrate (or retentate) are loaded. This represents a further concentration of approximately 4.5-fold. Thus, overall the concentration using the "PELLICON" AND "MINITAN" system in series gives a concentration of clarified crude media of approximately 180-fold. After each batch run both the "PELLICON" and "MINITAN" systems are washed with 5-10 L PBS.

The above system not only concentrates the clarified culture media, but also specifically purifies HBsAg particles from the media constituents. After concentration in above described systems with the 300,000 MW cut-off membrane only 2.5% of total clarified culture media protein is recovered. However, 95% of total HBsAg particles in the culture media are recovered. This represents a specific purification of HBsAg particles from culture media-derived contaminants (approx. 35-fold). Although 95% of original HBsAg particles are recovered, they constitute only part of the 2.5% original total protein recovered. That is, 95 mg HBsAg in a total of 636 mg protein (about 15%). The above 150 ml concentrate (MINITAN retentate) is therefore further purified by gel filtration to achieve final HBsAg particle purification (Steps 4, 5).

Step 4: Gel-filtration Purification of HBsAg Particles from Concentrated, Clarified Culture Media To further purify the HBsAg particles, applicant exploited their chemical-physical properties, namely their effective molecular weight which is in the $1-2\times10^6$ dalton range. For this reason "SEPHACRYL S-400("PHARMACIA) gel filtration columns are used which exclude molecules of molecular weight greater than $1\times10^6$ daltons. "SEPHACRYL S-400" is a gel filtration column of an allyl dextran covalently cross-linked with N,N' methylene bisacrylamide. Thus, large molecules such as HBsAg particles are excluded and are eluted rapidly. Smaller contaminating molecules such as albumin and other proteins enter the column resin and are eluted slowly, resulting in effective separation between HBsAg particles and low molecular weight contaminants. The "SEPHACRYL S-400" columns applicant uses are 2.6 cm×190 cm in size, with effective column bed volumes of 1 liter. For larger volumes of concentrate or larger amounts of protein in the concentrates, "SEPHACRYL S-400" columns of greater capacity may be employed.

The concentrated culture media in applicant's typical batches are about 150 mls in volume (Step 3) and contain about 95 mg HBsAg particles out of a total of about 640 mg protein. As a result of the dialysis step during concentration (Step 3), the concentrate is therefore a PBS solution containing HBsAg particles and contaminating proteins (i.e., 95 mg HBsAg in 150 ml PBS). For each batch of concentrate applicant employs only 1 "SEPHACRYL S-400" column, although more can be used to increase the rate of purification.

Applicant loads one-third (about 32 mg HBsAg in 50 ml PBS) of concentrate per gel filtration through the column. This represents about 5% (in volume) of the column bed volume. The flow rate is adjusted to about 10 cm per hour for best separations which results in a low operating pressure of about 25-30 cm $H_2O$.

Elution of HBsAg particles from the column is done by using up to 1 bed volume (1 liter) of PBS. After elution, and before re-use of the same column, the column is washed with 2-3 bed volumes (2-3 liters) of PBS.

Because of the large size of the HBsAg particle it does not enter the column bed resin, and is thus rapidly eluted from the column. The HBsAg particle peak is recovered in fractions that follow closely those of the void volume. Eluted fractions are usually 10 ml per fraction. Elution of HBsAg particles is consistently in 14-15 fractions (140-150 ml).

The recovery rates of HBsAg particles from the "SEPHACRYL S-400" column are very high and the degree of purification is considerable. From about 32 mg HBsAg loaded in 50 ml PBS, 30 mg HBsAg was recovered in 140 ml eluate, a recovery of 92%. Purification of HBsAg particles was 4-5 fold after 1 column run, the HBsAg—specific component of total protein is 60-70% for the eluted HBsAg peak fraction (an increase from only 15% of total in pre-column concentrate). To further purify the HBsAg particles to greater than 95% purity a second gel filtration through the same "SEPHACRYL S-400" column is done as described in step 5.

Step 5: Second Gel Filtration Purification of HBsAg Particles from Eluted Peak of First Gel Filtration Column The same "SEPHACRYL S-400" column used for the first gel filtration run (step 4) is used for the second gel filtration run. After the first gel filtration run the column is washed with 3-5 bed volumes (3-5 L) of PBS, to remove all bound molecules. Each typical batch of concentrated, clarified culture media requires 3-4 runs through the first column, each run being 1/3 the volume of the concentrate. For the second gel filtration run, the peak fractions of two first gel filtration runs are combined (140-150 ml each). Thus, typically, 280-300 ml of combined, eluted HBsAg particle peaks are first concentrated and then loaded on the Sephacryl S-400 ® column for the second gel filtration run. (The third first gel filtration eluted HBsAg peak, is combined with that of the next batch for the second gel filtration run. Thus, for every two batches of concentrated culture media containing HBsAg particles, 6 runs are required for the first gel filtration and 3 runs for the second gel filtration.)

To concentrate the combined eluted peaks before loading on the second gel filtration column, the "MINITAN" tangential flow ultrafiltration system with a 300,000 MW cut-off membrane is used (as described in step 3). This reduces the volume from 280-300 ml to about 60 ml (5-fold concentration.) This 60 ml contains about 57-60 mg HBsAg particles and is loaded on the "SEPHACRYL S-400" column for the second gel filtration run.

The HBsAg particle peak eluted (with PBS) from the second gel filtration run contains about 48.5 mg HBsAg particles in 140 ml PBS. This represents a recovery of 85% for HBsAg particles. Further, this second gel filtration peak contains more than 95% (about 98-99%) pure HBsAg-specific protein.

Thus, overall, using 2 subsequent gel-filtration columns to purify HBsAg particles from concentrated, clarified, crude media, applicant achieves a high yield (78%) and very high purity (greater than 95%).

Throughout the Purification Process, rates of recovery, yields, and purity of HBsAg particles, at each stage, were determined using the analytical methods described in Examples 7, 8 and 9.

The purification scheme is outlined in FIG. 4 and production and purification of a typical batch of HBsAg particles is represented in Example 6.

In the purification process described herein, Steps 1-5 can be scaled-up for commercial production of HBsAg particles to be used in vaccines. This is accomplished by:

(1) growing cultures in larger numbers of roller bottles or fermentors with microcarrier adaptors;
(2) ultrafiltration using "PELLICON" and "MINITAN" systems, or their equivalent, adapted for industrial scale volumes (Millipore ® Corp.); and
(3) gel filtration purification using "SEPHACRYL S-400" columns of larger bed volumes, or large numbers of described columns (steps 4, 5) connected in series.

Finally, some of the novel features of applicant's production and purification process may be summarized as follows.

Prefractionation of culture media removes troublesome high molecular weight protein contaminants enabling applicant to purify HBsAg particles in a much simplified manner. The concentration step prior to purification is highly efficient and accomplishes considerable pre-purification. The purification steps are rapid in a system that is re-usable.

All of the components comprising the clarification, concentration, and purification steps (Steps 2-5) can be linked together physically (with tubing) to form a closed system. As all of the components may be sterilized, applicant's purification process is carried out under sterile conditions throughout within a closed system.

Applicant therefore can produce large amounts of highly purified recombinant DNA-produced HBsAg particles with very high efficiency and very low cost.

EXAMPLE 6

Production and Purification of 100 mg HBsAg—First Batch

The methods described below for the production and purification of HBsAg particles are described in more detail in Example 5.

Twenty roller bottles were employed for production of HBsAg. The medium used contained the filtrate of FCS-supplemented culture media which had been prefractionated by "PELLICON" ultrafiltration with a 300,000 MW cut-off membrane Table 1 summarizes the results obtained from the first batch.

TABLE 1

| | First Batch Purification*** | | | | | | | |
|---|---|---|---|---|---|---|---|---|
| | | Total Protein | | | | Total HBsAg | | |
| Source | Vol. (L) | mg/ml | mg (total) | Recovery | ug/ml | mg (total) | Recovery | % HBsAg of total Protein |
| 1. Crude* | 25 | 1.0 | 25,000 | 100% | 4.04 | 101 | 100% | 0.4% |
| 2. Clarified Crude | 25 | 1.0 | 25,000 | 100% | 4.0 | 100 | 99% | 0.4% |
| 3. Concentrate** | 0.148 | 4.3 | 636 | 2.54% | 650 | 95.2 | 95.2 | 15% |

*Concentration of HBsAg in the Crude media was 4.0 mg/l. Crude Media refers to cell culture media collected daily and pooled until 25 l are accumulated at which stage purification is carried out. This media is clarified by Pellicon ® Ultrafiltration with a 0.22 micron membrane - clarified crude media.
**The clarified crude media was concentrated and dialyzed on Pellicon with a 300,000 MW cut -off membrane against 10 L PBS (10 × 1 L). The retentate on the filter - 660 ml - was further concentrated by Minitan ® (300,000 MW cut-off membrane) to 148 ml final concentrate. Note that specific purification of HBsAg particles is achieved by the concentration step.
***A second Batch of 100 mg was concentrated in the same way with similar results.

The concentrate was further purified by gel filtration on a "SEPHACRYL S-400" column (2.6×190 cm).

The column was loaded with 32.5 mg HBsAg (1/3 volume of concentrate). 30.0 mg HBsAg were recovered in 140 ml eluate (recovery of 92%). The eluates of two columns were combined, concentrated by MINI-TAN (300,000 MW cut-off membrane) to 58 ml and subjected to a second identical gel filtration run on the same "SEPHACRYL 400" column. From 57 mg HBsAg loaded on second column 48.5 mg were recovered (85%). HBsAg particles are purified 3-4 fold on the first column (from 15% to about 60% of total protein), and another 1.5 fold on the second column (from about 60% to more than 95% of total protein).

The purified HBsAg particles were analyzed by SDS-PAGE (15%). The HBsAg—specific protein bands were visualized by silver staining and Western blots, using rabbit antibodies as described in Example 7.

EXAMPLE 7

Analysis of Purified HBsAg Particles

A. The purity of the HBsAg particles after each step in the purification process (see Examples 5 and 6) was evaluated by SDS-PAGE (SDS polyacrylamide gel electrophoresis) (15% gels) and silver staining of the gels. The gels demonstrated that the HBsAg particles obtained after the second gel filtration step (Examples 5 and 6) were about 98-99% pure.

The following samples were compared by SDS-PAGE and silver staining: clarified crude culture media; concentrate of crude clarified media; concentrated eluate from the first "SEPHACRYL S-400" gel filtration; concentrated eluate from the second "SEPHACRYL S-400" gel filtration; and peak fraction of sucrose banded media concentrate (see Example 11). The same amount of protein, determined by standard methods, was loaded for each sample on the gel. In the crude media the major bands corresponded to contaminant protein (albumin), with HBsAg—specific protein bands being only minor bands. In the concentrated crude media the HBsAg —specific protein bands are enriched (15% of total) with a significant decline in contaminant bands. After the first "SEPHACRYL S-400" column the HBsAg—specific bands represent about 60% of protein bands, contaminant bands are minor bands at this stage. After the second "SEPHACRYL S-400" column all HBsAg—specific bands are clearly observed; 24K, 27K, 33K, 36K, 39K and 42K. They represent more than 95% of all protein bands. The major HBsAg-specific bands are 24K, 27K, 33K, and 36K with 39K and 42K being minor but significant bands. The sucrose-banded sample has a very similar profile to the first "SEPHACRYL S-400" column eluate illustrating that sucrose banding only achieves HBsAg particle purity of 60%.

B. The purified HBsAg particles, after each step in the purification process (Examples 5 and 6) were further analyzed by Western blots using rabbit antibodies made against plasma-derived HBsAg particles. The blots demonstrated the presence of six major protein bands specific to HBsAg particles with the following molecular weights 24K, 27K, 33K, 36K, 39K, 42K.

The Western blot technique using HBsAg particle-specific antibodies permits the specific identification of HBsAg particle bands. The same amount of protein for each sample was used. The antibodies used also had anti-albumin specificity. This was useful in determining the specific reduction of albumin, the major protein contaminant, throughout the purification process.

The crude media sample showed only the albumin band clearly, HBsAg particle-specific bands being below the level of detection using this method. For antibody-specific detection of protein bands both the amount of protein per band and their antigenicity under the assay conditions determine the levels of detection. Applicant concludes that the crude media contain very low amounts of HBsAg particle -specific bands (as observed in A by silver staining whose level of detection is about 50 ng/band) and these bands do not have high antigenicity in our assay conditions. The media concentrate sample had reduced levels of albumin and HBsAg-specific bands 24 K and 33K are major bands with 27K and 36K as minor bands. In the first "SEPHACRYL S-400" column eluate albumin is only a minor band and the HBsAg-specific bands 24K and 33K are major bands with 27K, 26K, 39K and 42K as minor bands. The sucrose banding sample has a very similar profile to the first "SEPHACRYL S-400" column eluate. The second "SEPHACRYL S-400" column eluate has almost no albumin band observable HBsAg-specific bands 24K, 27K, 33K are major bands and 36K, 39K, 42K are minor but significant bands. In this sample, therefore, the bands are almost entirely HBsAg particle-specific indicating their very high purity. This therefore confirms the results observed in A above using silver staining of gels.

Further evaluation of the band intensity of the Western blots (especially for the samples corresponding to the first and second SEPHACRYL S-400" column eluates) shows the stoichiometry of HBsAg-particles produced and purified by applicant's method: that is, 24K, 27K, and 33K are major bands and 36K, 39K and 42K are minor bands.

These findings are in full agreement with the data of Heermann et al., J. Virol. 52: 396-402 (1984), who described the following proteins in blood plasma-derived HBV particles and large filaments which contain only HBsAg. (The smaller 20 nm HBsAg particles that they describe do not contain 39K and 42K).

| | |
|---|---|
| 24 K - Non-glycosylated | (S) |
| 27 K - Glycosylated | (S) |
| 33 K - Single Glycosylated | (Pre-S2) |
| 36 K - Double Glycosylated | (Pre-S2) |
| 39 K - Non-Glycosylated | (Pre-S1) |
| 42 K - Glycosylated | (Pre-S1) |

It should be noted that in applicant's comparison between the silver stained gel and the Western blot using rabbit antibodies an increased immunogenicity of the Pre-S2 33K protein of the HBsAg particles is observed. On the silver stained gel the 33K band is minor in comparison to the 24K and 27K major bands. On the Western immunoblot the 33K band is major with respect to the 24K and 27K major bands. This agrees with the findings of increased immunogenicity associated with Pre-S2 region determinants discussed, where noted, in the 'Background to Invention', e.g., Milich et al., J. Immunol. 137: 315–322 (1986).

C. The presence of Pre-S1 proteins (39K, 42K) was further demonstrated by using specific monoclonal antibodies against the Pre-S1 region by the Western blot technique. The blots demonstrate at least two-fold higher amounts of non-glycosylated Pre-S1 39K, than the glycosylated form 42K. (This assumes that monoclonal antibodies react equally with glycosylated and non-glycosylated proteins.)

D. The purified HBsAg was further evaluated for the presence of contaminants originating from the FCS and the CHO cells. By using the Western blot technique with two rabbit antibodies against FCS and CHO cell proteins respectively, it was possible to demonstrate that the contaminant level in the purified HBsAg was below detection level in both cases when compared to positive controls. The detection level referred to here is both the amount of protein per band and its antigenicity in the assay conditions.

EXAMPLE 8

A. Solid Phase Radioimmunoassay for HBsAg Particles Produced by Applicant's Novel Production-Purification Process (Described in Examples 5 and 6)

Figures 6A, 6B:
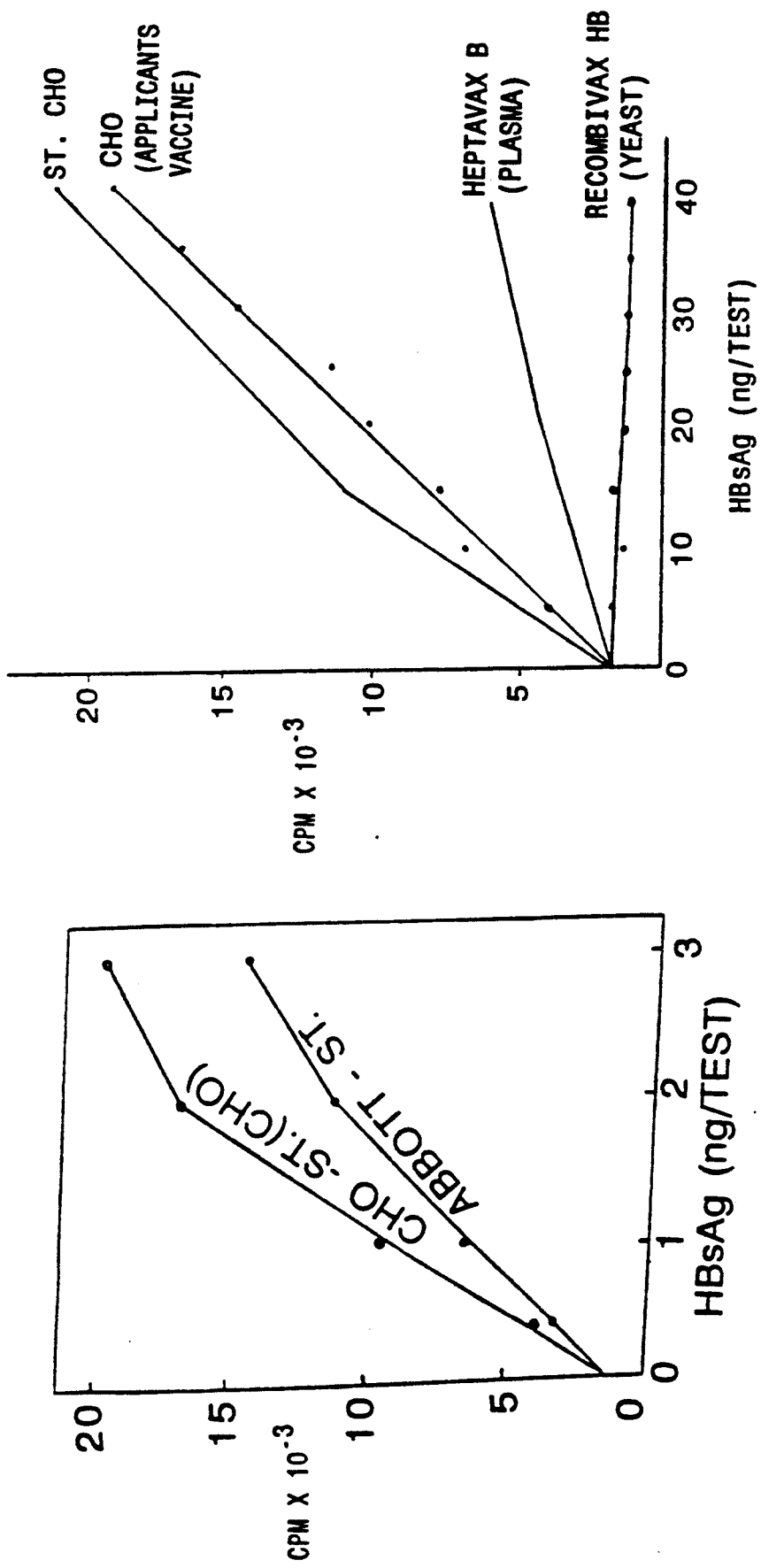
FIG. 6: Solid phase radioimmunoassay for HBsAg: A solid phase radioimmunoassay kit (Travenol) was used.

For HBsAg particle immunogenicity determination a solid phase radioimmunoassay kit for detection of HBsAg (TRAVENOL) was used. The HBsAg particles applicant assayed were those of the concentrated second gel filtration eluate (Example 5, Step 5 or FIG. 4, Step 5). The kit was calibrated against known standards (ABBOTT). The calibration curve of applicant's recombinant DNA-produced HBsAg (CHO) was compared to the ABBOTT calibration curve. It seems that applicant's HBsAg (CHO) has higher affinity to the chimpanzee antibodies from the TRAVENOL kit as compared to the ABBOTT standard (FIG. 6 A).

B. The Calibration Curve of Recombinant HBsAg Vaccine Produced in CHO Cells by Applicant's Novel production -Purification Process (Example 5)

Applicant prepared his HBsAg vaccine by the methods described in the following Example 9, by conjugating the highly purified HBsAg particles (concentrated HBsAg particles obtained from Step 5 in Example 5) with an Alum adjuvant preparation.

Applicant's HBsAg vaccine was compared to calibration curves of both the plasma derived (HBsAg) vaccine-HEPTAVAX B and the yeast recombinant vaccine-RECOMBIVAX HB. The results demonstrate again that applicant's vaccine (CHO) has the highest affinity to the chimpanzee antibodies from the TRAVENOL kit, as compared to the commercially available vaccines ("HEPTAVAX," RECOMIBVAX"). It seems that the recombinant yeast vaccine RECOMBIVAX HB does not react in the assay, probably due to very low affinity to the antibodies of the TRAVENOL RIA kit.

EXAMPLE 9

Seroconversion in Small Animals (Mouse)

A. HBsAg Potency Assay by Seroconversion in Mice

Hepatitis B surface antigen (HBsAg) produced by CHO-HB200 cells (Examples 3 and 4) was highly purified (about 98%) (Examples 5 and 6). The HBsAg concentration was determined with solid phase radioimmunoassay kit for detection of HBsAg ("TRAVENOL") and by protein determination (Examples 7 and 8). The HBsAg was complexed with an alum adjuvant, constituting a recombinant HBsAg vaccine. The alum preparation was carried out by titration of 1.5 ml of a 10% solution of alum (aluminum potassium sulfate 18 $H_2O$) with an excess of 1 M sodium phosphate ($Na_2HPO_4$) (about 1 ml). The resulting suspension was diluted tenfold with $H_2O$ and centrifuged. The alum sediment was resuspended in 10 ml of PBS to give a solution of approximately 2.5 mg/ml of $Al(OH)_3$. To 1 ml of this solution, 50 μg (micrograms) of applicant's recombinant CHO HBsAg was added, and the volume was adjusted to 5 ml with PBS.

Applicant's recombinant vaccine (CHO) was compared with a plasma-derived vaccine-HEPTAVAX (Merck, Sharp and Dohme) and a yeast recombinant vaccine-"RECOMBIVAX HB" (Merck, Sharp and Dohme).

Balb/c mice were injected intraperitoneally with 1 ml vaccine samples each containing the following amounts of HBsAg: 0.01 μg, 0.03 μg, 0.09 μg, 0.27 μg, 0.81 μg, 2.4 μg. (10 mice per group). Thirty days after injection the mice were exsanguinated and the serum was tested for the presence of anti-HBsAg antibodies by the "HUSAB EIA" Kit ("ABBOTT") and calibrated against reference serum (WHO) received from the Dutch central blood bank.

The results are summarized in FIG. 7. It can be deduced that applicant's recombinant (CHO) vaccine has at least ten-fold higher potency as compared to the two commercial vaccines available on the market.

The above experiments were repeated on a larger scale using a preparation of applicant's recombinant (CHO) vaccine prepared by the especially preferred method detailed in Example 11. Similar results to those described above were obtained.

B. Evaluation of the Quality of Antibodies Elicited in the Seroconversion Assay (as described above in A)

Three kinds of antibodies were elicited in the mouse seroconversion assay:
(a) antibodies against Heptavax B ® (plasma)
(b) antibodies against Recombivax HB ® (yeast)
(c) antibodies against applicant's vaccine (CHO).
The three types of antibodies were analyzed for quality and specificity at the same titer. Applicant's highly purified HBsAg (CHO) particles (Example 5, Step 5) were fractionated by electrophoresis on SDS polyacrylamide gel and transferred to nitrocellulose filters. Using the Western blot technique, the filters were exposed to the three types of antibodies.

The mouse antibodies against "HEPTAVAX B" (plasma) and "RECOMBIVAX HB" (yeast) recognized only the S protein (24K) present in the HBsAg particles, while mouse antibodies against applicant's vaccine (CHO) recognized both the S and Pre-S2 (24K, 33K) proteins.

These findings demonstrate again that the vaccine elicited higher titers of antibodies as compared to commercial vaccines. Moreover, the quality and specificity of antibodies elicited against applicant's vaccine were different as they recognized, in addition to the S (24K) protein, the Pre-S2 (33K) protein which is considered important for viral infectivity.

C. Experiments with Non-Responding Mice

Experiments were carried out with congenic mice strain B10s (obtained from Harlan Olac Ltd., Bicester, U.K.) which are known to be non-responders to the S protein, i.e., they do not respond to any HBsAg vaccine which does not contain Pre-S proteins (Milich et al., Science 228: 1195-1198 (1985)). The mice were divided into two groups of 26 mice per group. One group of mice was injected intraperitoneally with 1 μg of the yeast-derived "RECOMBIVAX HB" vaccine (described in the Background of the Invention) which has no Pre-S1 or Pre-S2 determinants, and the other group of mice was injected intraperitoneally with 1 μg of applicant's HBsAg vaccine produced as described in Example 11; (this is about 50 times the normal dose for mice). Thirty days after primary immunization half the mice in each group were exsanguinated and antibody titers in the serum were measured as described below. The remaining mice were immunized again (booster) and two weeks after secondary immunization they were exsanguinated and antibody titers in the serum were measured as described below.

The serum was analyzed using a commercial assay for anti-HBsAg antibodies, "AUSAB EIA" ("ABBOTT"); this assay detects and quantitates anti-S antibodies. The results, shown in FIG. 10, demonstrate that after primary immunization there is only a small rise in the antibody titers in both groups of mice. However, after secondary immunization, applicant's vaccine elicited antibody titers almost ten times higher than did the "RECOMBIVAX"; this is a statistically significant difference ($p<0.001$). These results show that applicant's vaccine should overcome the problem of non-responsiveness which occurs with existing vaccines D. Further Evaluation of the Quality of Antibodies Elicited in the Seroconversion Assay In further experiments, the above sera of the non-responder mice, that were collected following a second immunization with yeast-derived "RECOMBIVAX HB" and the applicant's HBsAg vaccines, were assayed for the presence of anti-Pre-S1 antibodies, by a solid-phase ELISA. In this assay, a synthetic peptide of 21 mer corresponding to the Pre-S1 region of HBsAg was coated onto polystyrene 96-well microtiter plates (Nunc, Covalink plates, Cat. #478042), at 0.5 μg/well. Wells were then layered in duplicates at a 1:5 dilution with the different sera, including normal mouse serum as a negative control. This was followed by successive incubations with biotinylated anti-mouse affinity purified IgG as second antibody and ExtrAvidin peroxidase (Bio-Makor staining kit, Cat. #7801-1). The results (shown in Table III below) indicate the presence of anti-Pre-S1 antibodies in sera of non-responder mice immunized with applicant's HBsAg vaccine, in comparison to the absence of such antibodies in sera of mice vaccinated with the yeast-derived "RECOMBIVAX" vaccine.

TABLE 3

Results of a SoLid-Phase ELISA for Anti-Pre-S1 Antibodies in Non-Responder Mice

| Source of Serum | O.D. (at 405 nm) | |
| --- | --- | --- |
| | Experiment 1 | Experiment 2 |
| After Applicant's Vaccine | 0.797; 0.811 | 0.608; 0.575 |
| After Recombivax | 0.422; 0.399 | 0.363; 0.352 |
| Normal Mouse Serum | 0.397; 0.399 | 0.389; 0.386 |

These results demonstrate that applicant's vaccine elicits the production of anti-Pre-S1 antibodies, whereas the yeast-derived vaccine elicits no such antibody production. The novelty and significance of these findings is discussed at the end of Example 12.

EXAMPLE 10

Alternative Methods for Purifying HBsAg Particles Secreted by Mammalian Cell Culture As illustrated in FIG. 4, the "Purification Scheme of HBsAg Particles" consists of five key steps. At each step alternative methods may be employed, other than those described in detail in Example 5.

Further, various combinations of alternate methods may be carried out to produce purified HBsAg particles.

A comparison of these alternative methods, to those of applicant's preferred purification process (described in Example 5 and FIG. 4) is summarized in Table 2 found at the end of this Example.

The following is a detailed description of possible alternative methods for each step of the purification scheme:

A. Alternative Methods to Step 1 (Prefractionation of culture media)

CHO cells producing HBsAg particles (described in Examples 3 and 4) may be grown alternatively in the following media:

1. Growth media described in Example 3(a) having between 2-10% fetal calf serum (FCS), preferably 2% FCS, without prefractionation of the growth media. (Prefractionation of the growth media is described in Example 5).

This alternative method, however, resulted in problems of further purification.

When culture media were not pre-fractionated, the levels of contaminating proteins in the subsequent purification steps was very high, the final yield was reduced and the purity of the final product was reduced. Alternative purification steps described in the following steps including the use of PEG fractionation; affinity chromatography ("AFFIGEL BLUE,", BLUE-SEPHAROSE" "PHENYL-SEPHAROSE"); Ion-exchange chromatography ("HEPARIN-SEPHAROSE" "DEAE-SEPHACEL"); and gel filtration ("SEPHACRYL S-400); were all used in combination with a first step of non-prefractionation of culture media. Only the gel filtration ("SEPHACRYL S-400) alternative was carried out on pre-fractionated culture media-produced HBsAg particles, preferred method A (Example 5).

2) Growth media described in Example (3) and Example 5, having between 2-10% FCS, preferably 2%, which had been pre-fractionated by "PELLICON" ultrafiltration (Example 5), but where said prefractionation employed a 10,000 MW or a 100,000 MW cut-off membrane instead of a 300,000 cut-off membrane.

This alternative method, however, resulted in problems of cell culture growth.

When a 10,000 MW or a 100,000 MW cut-off membrane was used in the "PELLICON" ultrafiltration prefractionation of culture media, cell growth was inhibited significantly resulting in lower yields of HBsAg.

Thus, applicant's preferred method for Step 1 is that described in FIG. 4 and Example 5.

B. Alternative Methods to Step 2 (Clarification of Culture Media Containing HBsAg Particles)

The culture media of CHO cells producing HBsAg particles which are secreted into the media may be clarified using the possible alternative steps:

1) Centrifugation of collected media in 1 liter buckets using a SORVALL centrifuge (Model RC-3B, with swinging bucket rotor) was at 4,000 rpm for 15-20 minutes. The supernatant (clarified of cells and part of the cell debris) is then subsequently processed according to steps 3-5 of purification process illustrated in FIG. 4.

Using these alternative methods, however, resulted in the following problems.

Centrifugation of harvested media only removed whole cells from the media, other major contaminants such as cell membranes and lipid complexes remained in the supernatant. This interfered with the subsequent gel-filtration purification steps (Steps 4, 5), leading to reduced overall yields of HBsAg particles and decreased HBsAg particle purity. Further, the centrifugation step is a time-consuming process and cannot be employed efficiently for large volumes (can process only approximately 12 liters/hour per centrifuge).

2) Filtration using a 0.22 micron filter system commonly used for sterilization purposes ("MILLIPORE"). (this is different to tangential flow ultrafiltration PELLICON system using a 0.22 micron membrane-Example 5).

Using this alternative method resulted, however, in the following problems.

Filtration using the 0.22 micron membrane sterilization system (as opposed to tangential flow ultrafiltration PELLICON System with a 0.22 micron cut-off membrane) gave efficient clarification of the media, removing whole cells, cell membranes and lipid complexes, but had the following drawbacks: this system cannot process large volumes because the 0.22 micron sterilizing-type membranes become clogged up rapidly and require frequent replacement This leads to losses in product yield and is time-consuming.

Thus, applicant's preferred system is that described in step 2 of FIG. 4 and Example 5. Here, applicant employs the tangential flow "PELLICON" ultrafiltration system with a 0.22 micron cut-off membrane. This is an industrial scale system, it can process large volumes of media and processing of media is rapid (several hundred liters per hour). The system is more resistant to clogging, and gives 100% recovery of HBsAg particles.

C. Alternative Methods to Step 3 (Concentration Step of Clarified Culture Media)

1) Polyethylene glycol (PEG) fractionation using 10% PEG (PEG 6000 Sigma) to precipitate high molecular weight protein complexes which include the HBsAg particles. PEG dissolved in PBS in concentrated form (25%–30%) is added to the clarified culture medium (Step 2) such that the final concentration of PEG is 10% w/v. The PEG precipitate can be collected by centrifugation (in Sorvall ® RC-38 centrifuge, fixed angle rotor, in 50 ml tubes at 6000–7000 rpm for 20 minutes) or by filtration using the "PELLICON" tangential flow ultrafiltration system with a 300,000 MW cut-off membrane (as described in FIG. 4, Step 3 and Example 5). The solution is mixed well and left for at least 30 minutes at 4° C. Note that this PEG fractionation step was only carried out with HBsAg particles produced in media which were not pre-fractionated in Step 1.

The following results were obtained using this alternative concentrating method.

10% PEG fractionation of clarified medium was efficient only when small volumes (up to 1 L) of clarified culture medium was used. Further, more importantly, the PEG fractionation only gave 75% recovery of HBsAg particles. 10% PEG fractionation leads to a loss of approximately 80% of the total protein (which includes 25% of total HBsAg particles) and the purity of HBsAg particles is only 0.5–1% after this 10% PEG fractionation. Finally, after PEG fractionation, the HBsAg-containing precipitate must be resuspended in PBS and dialyzed to remove the PEG. This step must be followed subsequently by another concentration step prior to final steps of purification (Steps 4, 5). Thus, PEG fractionation is time-consuming, results in a significant loss of HBsAg particles, is at best a preconcentrating step requiring subsequent concentration steps and taken together, it can be considered an expensive step. Note that PEG concentration was carried out in combination with alternative methods to some of the following steps (i.e. together with ion-exchange chromatography, affinity chromatography and gel filtration).

2) Tangential-flow ultrafiltration using either 10,000 MW 100,000 MW or 300,000 MW cut-off membranes ("MINITAN", "PELLICON" systems made by "MILLIPORE"). These methods using the "MINITAN" or "PELLICON" system permit dialysis of the retentate (material that does not pass through the membranes) during the ultrafiltration process. Typical application of this system are as follows:

a) MINITAN system with 10,000 MW cut-off membrane: 6.4 L of clarified culture medium (step 2) ultrafiltered and dialyzed with 2 L of phosphate-buffered saline (PBS) (4×500 ml PBS). This yielded 260 ml final concentrate (approx. 25-fold concentration).

b) Pellicon ® system with 100,000 MW cut-off membrane: 34 L of clarified culture medium (step 2) ultrafiltered and dialyzed with 8 L of PBS (8×1 L PBS). This yielded 660 ml of final concentrate (approx. 50 fold concentration).

c) Pellicon ® system with 300,000 MW cut-off membrane: 34 L of clarified culture medium (step 2) ultrafiltered and dialyzed with 10 L of PBS (10×1 L PBS). This yielded 500 ml of final concentrate (approximately 70 fold concentration).

The following results were obtained using alternative concentrating methods.

a) Ultrafiltration and dialysis with the MINITAN employing a 10,000 MW cut-off membrane was slow; this system is thus not applicable for industrial-scale production of HBsAg particles. While recovery of HBsAg particles was very high (more than 96%) total protein recovery was also very high (more than 95%). Therefore, this system is very effective in concentrating the starting material without loss of product but is unable to purify HBsAg particles from the starting material, the ratio of HBsAg particles to total protein remaining the same (purity of HBsAg particles is only about 0.4%).

When the volume of clarified media was increased, the amount of protein retained on the membrane increased to the extent that the rate of flow decreased substantially.

b) Ultrafiltration and dialysis with the "PELLICON" system employing a 100,000 MW membrane is more efficient than described above (a) using the Minitan ® system with a 100,000 MW cut-off membrane. Larger volumes could be processed and the rate of flow is greater. Less protein is retained on the membrane and thus flow rate is not restricted severely when large volumes of media, having large amounts of protein, are processed.

However, although the concentration of culture media is very effective, this system cannot purify specifically HBsAg particles: recovery of HBsAg particles was 100% while total protein recovery was more than 95%. Thus, the ratio of HBsAg particles to total protein remains the same as in the starting material (purity of HBsAg particles is only abut 0.4%).

c) Ultrafiltration and dialysis with the "PELLICON" system employing a 300,000 MW membrane is the preferred method, being more effective than both above described methods (a, b). Here, the system achieved both concentration and specific purification of HBsAg particles: 98% of HBsAg particles were recovered while only 10% of the original total protein was recovered. This increased the ratio of HBsAg to total protein by a factor of 9 (purity of HBsAg particles is 3–4%).

d) To achieve further purification of HBsAg at this concentration step applicant added another optional, alternative step which is subsequent to ultrafiltration and dialysis using the above described Pellicon ® system with a 300,000 MW cut-off membrane. This additional step is PEG fractionation with 10% PEG. (The method is as described in part 1 of this section but differs because here PEG is used after ultrafiltration and not instead of ultrafiltration). This, however, resulted in a 28% reduction in recovery of HBsAg particles (70% recovery from 98%), although reduction of total protein to the desired level of 2.5% (from 10%) was achieved. (Purity of HBsAg particles is about 7–10%). This alternative step of PEG fractionation after ultrafiltration was not attempted for alternative systems described in a and b above because of their very high total protein content (more than 98%) after ultrafiltration.

To sum up, the concentration step is a critical step in the purification process. It is essential to concentrate clarified culture media before final purification employing gel filtration (Example 5, FIG. 4) can be carried out. Note that all of the above-described alternative concentration methods were applied to clarified crude culture media which were not pre-fractionated at the time of cell culture. Prefractionation of said culture-media using the described system (step 1, FIG. 4, Example 5) was developed as a unique step to overcome the problems encountered during steps of concentration (Step 3) and final purification (Steps 4, 5). Said prefractionation removes culture medium contaminants (before cell culture) whose molecular weights are about 300,000.

Applicant's preferred method of concentration (Example 5, FIG. 4) employing the Pellicon ® system with a 300,000 MW cut-off membrane, when carried out on clarified crude media which was originally pre-fractionated gave the following results: from 25 L of media 148 ml of concentrate was obtained (dialysis with PBS during ultrafiltration concentration was with 10 L PBS). This is a concentration of 170 fold and recovery of HBsAg is approximately 96% while total protein recovery is only 2.5%, the desired level. (Purity of HBsAg particles at this stage is about 15%—see also Table I.) This is thus far superior to all alternative steps described above (1, 2a, 2b, 2c, 2d). Applicant's preferred method is thus one that achieves both concentration and purification of HBsAg to a high level in one step, without significant loss of HBsAg particles.

D. Alternative Methods to Steps 4 and 5 (Gel Filtration Purification)

1) Affinity Chromatography Using Hydrophobic Columns

Three types of affinity columns were used: "BLUE-SEPHAROSE" "PHARMACIA", "AFFIGEL BLUE" "BIORAD", AND "PHENYL-SEPHAROSE" ("PHARMACIA"). (Use of the columns was ACCORDING to specification sheets supplied by "PHARMACIA" and "BIORAD".)

The "AFFIGEL BLUE" and "BLUE-SEPHAROSE" columns were used in the following purification process (in combination with various alternative steps to applicant's preferred process).

HBsAg particles were derived from cultures whose media were not pre-fractionated, and which were concentrated with 10% PEG (see above Section C 1, alternatives to concentration step). The PEG precipitate was dissolved in a minimal volume of PBS (250 μg protein per ml PBS) and loaded onto either "AFFIGEL BLUE" or "BLUE-SEPHAROSE" columns. Applicant used packed 35 ml columns and loaded 5 ml HBsAg in PBS per column (1.25 mg HBsAg particles per column). The columns were washed with 2 volumes (70 ml) PBS and eluted with a sodium thiocyanide buffer (NaSCN), followed by 40% PEG solution in PBS. Elution was carried out by first washing with 1 volume (35 ml) of 0.1 NaSCN Buffer, followed by a second wash with 0.25 M NaSCN (35 ml). This was effective in removing proteins such as albumin without removing HBsAg from the column. HBsAg particles were eluted from the column with a 40% PEG solution with 1 M NaCl in PBS. Only 10–20% of HBsAg particles were recovered by this method, with no difference apparent between either the Affigel Blue ®or "BLUE-SEPHAROSE" columns. HBsAg purity was low (5%–7%) as it was co-eluted with albumin. The "PHENYL-SEPHAROSE" column (a 2.7 ml bed volume mini column) was used in the following purification process: HBsAg particles were derived from cell cultures whose media were not pre-fractionated and were concentrated and dialyzed against PBS on a Pellicon ® 300,000 MW cut-off membrane. This was further concentrated with 10% PEG in PBS and the PEG precipitate dissolved in a minimal volume of PBS (1.8 ml final volume, about 0.5 mg HBsAg particles). This was then loaded onto the column which was washed with 19 ml PBS (7 volumes). Elution was with 13.5 ml H$_2$O (5 volumes). Only 22% of the HBsAg was eluted and it was of low purity (7%) as albumin was co-eluted with the HBsA fraction.

These methods are therefore inferior to applicant's preferred process (Example 5, FIG. 4).

2) Ion-Exchange Chromatograph

Two types of ion-exchange columns were used: HEPARIN-SEPHAROSE 3 ml bed volume column ("PHARMACIA") AND "DEAE-SEPHACEL", 2.5 ml bed volume column ("PHARMACIA") (columns were used according to the supplied specifications of the manufacturer, "PHARMACIA").

For both columns the loaded HBsAg particle sample was prepared in the following way:

HBsAg particles were derived from cultures whose media was not pre-fractionated. The collected culture media was concentrated and dialyzed on a "PELLICON" 300,000 cut-off membrane and further concentrated with 10% PEG in PBS. The PEG concentrate (HBsAg sample) was dissolved in dilute PBS (0.3×PBS) and loaded onto the columns in the following way:

6 ml HBsAg sample (about 1.5 mg) was loaded onto the "HEPARIN-SEPHAROSE" column. 11 ml (about 2.75 mg) was loaded onto the "DEAE-SEPHACEL" column. Elution of HBsAg particles from the columns was as follows:

The "HEPARIN-SEPHAROSE" column was washed with 4 volumes (12 ml) 0.3×PBS and eluted with a PBS gradient solution of between 0.3×PBS and 2×PBS (30 ml=10 volumes). Only 10%-20% of HBsAg was recovered from this column and it was of low purity (5%-7%). The "DEAE-SEPHACEL" column was eluted by a step-wise PBS gradient solution; 1 volume (2.5 ml) each of 0.2 PBS, 0.3×PBS, 0.5×PBS, 0.75×PBS, 1×PBS, 1.5 ×PBS, 2×PBS, were used to wash the column. This enabled release of HBsAg particles, recovery was 70% but was spread over many fractions (a smear). Further, the purity was low (about 5-10%) as contaminants were present in all HBsAg fractions.

Thus, purification of HBsAg particles was not effective with these methods.

Note that subsequently several other ion-exchange columns were tested (see Example 11). The use of "SP-TRISACRYL" gave unexpectedly good results and the column was incorporated into preferred method B (Example 11).

3) Gel-Filtration Chromatography a) As an alternative to the preferred "SEPHACRYL S-400" gel filtration, "SEPHAROSE CL-6B" ("PHARMACIA") was employed (500 ml bed volume column, used according to manufacturer's specifications).

Gel filtration using the "SEPHAROSE CL-6B" column was compared directly with the "SEPHAROSE S-400" column (a 500 ml bed volume type in this method) in the following way:

HBsAg particles were derived from cultures whose media was not pre-fractionated. The harvested HBsAg-containing, culture media was first concentrated on a "PELLICON" 300,000 MW cut-off membrane or an "AMICON XM300", 300,000 MW cut-off membrane (Amicon Corp.), and then fractionated with 10% PEG (this reduces loss of HBsAg particles when compared to fractionation with PEG without prior concentration on "PELLICON" 300,000 MW cut-off membrane). The Pellicon ® or "AMICON" XM300 ®gave the same results. The PEG precipitate (HBsAg particle-containing sample) was dissolved in 1×PBS, preferably or in high salt Tris-NaCl Buffer (50 mM Tris-Trizma Base, Sigma; 3 M NaCl-Analytical, Merck). 8.1 ml HBsAg sample (about 2 mg) was loaded on either the SEPHAROSE or "SEPHACRYL" columns. In both cases sample loaded in PBS buffer was better (twofold) separated and purified than sample loaded in TrisNaCl buffer. The differences between the columns in purifying HBsAg particles may be summarized as follows:

HBsAg particles were eluted by washing the columns with 1 vol (500 ml) of PBS (both columns were 500 ml bed volume type columns). Eluted fractions were collected in 10 ml samples, aliquots of which were tested for HBsAg-specificity "TRAVENOL" kit—described in Examples 8 and 9 and protein determinations described in Example 7). The recovery (yield) of HBsAg particles was more than 90% from the "SEPHACRYL S-400" column and only 75% for the "SEPHAROSE CL-6B". Particle purity was 45% from the "SEPHARCRYL" column when sample was loaded in PBS (and 20% when loading was with Tris-NaCl buffer); while only 20-30% purity was achieved with the Sepharose ® a column when sample was loaded in PBS (10-15% purity when sample loaded in Tris-NaCl buffer).

To achieve greater purity of HBsAg particles using either the "SEPHACRYL" or "SEPHAROSE" columns a second gel filtration was carried out. Eluted peak fractions from the first gel filtration were concentrated with 10% PEG in PBS and PEG precipitates redissolved in PBS. Loading samples onto the second column was carried out as described above, for the first column but this time only PBS was used as loading buffer. HBsAg particles were eluted with and analyzed as above for the first column. The following was observed:

When the first column was "SEPHACRYL S-400" and the second column was "SEPHACRYL S-400", about 95% of HBsAg particles were recovered with a 60-70% purity.

When the first column was "SEPHACRYL S-400" and the second column was "SEPHAROSE CL-6B", only about 60-70% of HBsAg particles were recovered with only about 50% purity.

When the first column was "SEPHAROSE CL-6B" and the second column was "SEPHAROSE CL-6B", only 70% of HBsAg particles were recovered in a very broad peak (smeared peak) with a low purity of about 30%.

It should be noted again that these above described purification processes were carried out on HBsAg particles produced in cultures whose media were not pre-fractionated. The prefractionation step enables applicant to purify HBsAg particles to a much higher level, without the need for PEG fractionation/concentration at any stage, using only the steps described in Example 5 and FIG. 4. As described in Section C 1 of this Example (Alternative Methods to Step 3) PEG fractionation/concentration requires centrifugation and/or ultrafiltration with dialysis as an integral step. This is thus both time-consuming and increases production costs.

Finally, as described above, preparation of HBsAg samples to be purified by gel filtration used a step of concentration with either "PELLICON" or "AMICON XM300" system with 300,000 MW cut-off membranes. Both achieved the same results, but the "AMICON" system used could only process 50-ml samples and required 50 psi operating pressure. The "PELLICON" system can process far greater volumes and operates at 0 psi pressure. This is desirable for industrial applications and for low cost production.

Thus, the preferred method is two consecutive column runs using "SEPHACRYL S-400" for HBsAg preparations which were derived from cell cultures whose media was pre-fractionated. This results in final HBsAg particle purity of greater than 95% after the second run (Example 5 and FIG. 4). This step is also more economical as the same column is employed for the two consecutive runs.

4) As another alternative to the second gel filtration step (Step 5 in FIG. 4 and Example 5), HBsAg particles eluted from the first "SEPHACRYL S-400" column (Step 4) were loaded onto a sucrose gradient as follows:

HBsAg particles were derived from cultures whose media were pre-fractionated. The HBsAg-containing media was processed as described in Example 5 up to the end of Step 4 (i.e. steps 1-4 inclusive).

Figure 5:
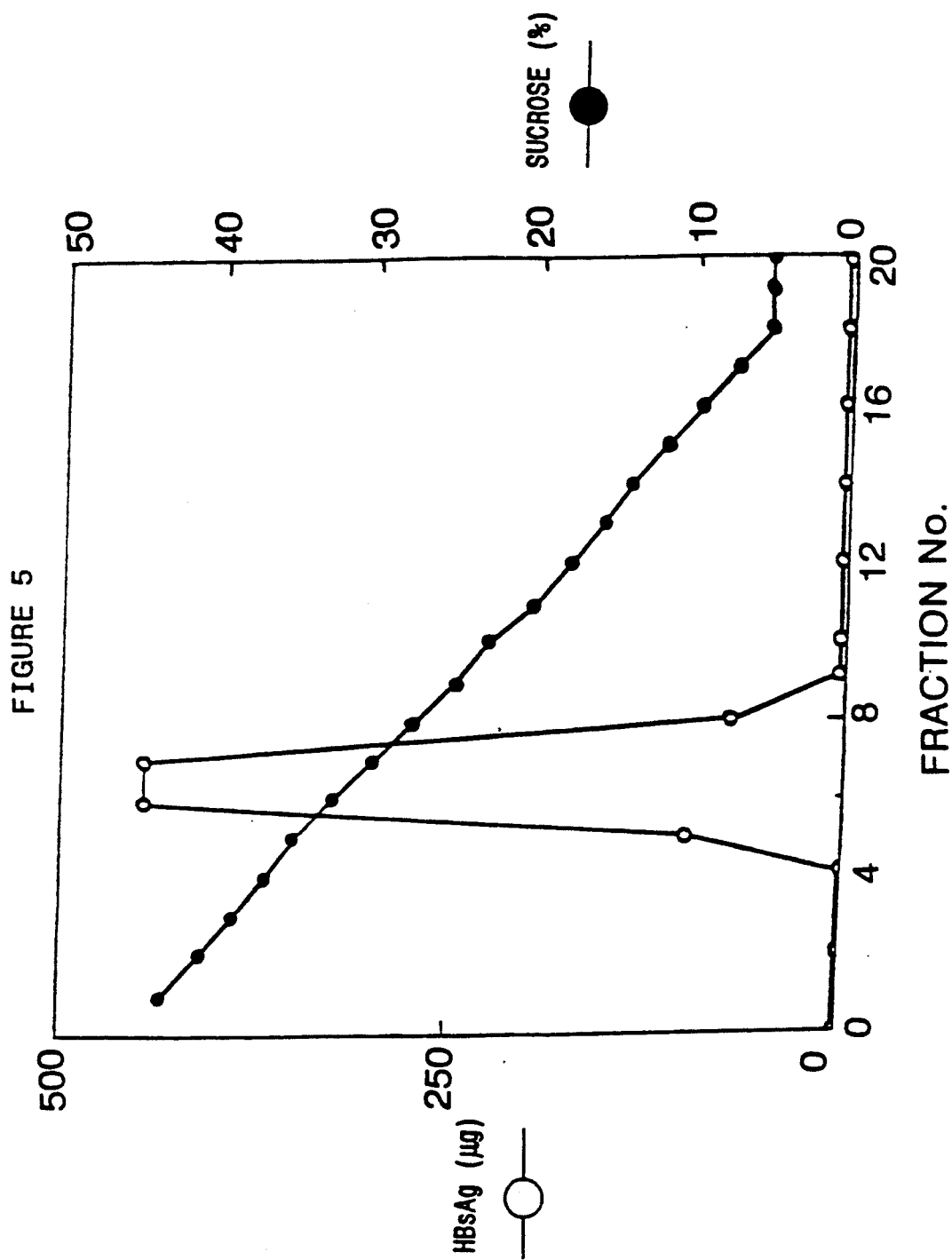
FIG. 5: Sucrose banding of HBsAg—purified HBsAg particles. The particles were loaded on a Sucrose gradient between 50–5% sucrose, ultracentrifuged in BECKMAN SW 27 rotor at 27000 rpm at 16–21° C. for 18 hours. 1.8 ml fractions pooled from the bottom were analyzed for HBsAg presence and sucrose concentration (refractometer).

Purified HBsAg particles (after gel filtration on first Sephacryl S-400 ® column) were loaded on a 50% to 5% sucrose gradient (made with PBS) in Beckman SW27 ultracentrifugation tubes. The sucrose gradient was ultracentrifuged at 27,000 rpm at 16-21° C. for 18 hours. After centrifugation 1.8 ml fractions were collected from the bottom of the tube, and their sucrose concentration (using a refractometer) and HBsAg-specificity were determined (using methods of Example 7). The HBsAg particle-specific peak was located as a sharp peak in fractions 6–7. This banding pattern of HBsAg in the sucrose gradient indicates the high homogeneity of the HBsAg particles, produced by applicant's method (illustrated in FIG. 5).

Further evaluation (described in detail in Example 7) of HBsAg purity after sucrose banding demonstrated no improvement in the purity (60–70%) of the HBsAg particles prepared by this method (as described in Example 7 after SDS-PAGE and Western blot analysis). Further, yields are also less than that achieved using gel filtration—only about 70% recovery. In addition, the sucrose method is very time-consuming and employs the use of expensive machinery.

5) As another possible alternative to a second gel-filtration step (Step 5 in FIG. 4 and Example 5) to achieve HBsAg particles of high purity, HBsAg particles eluted from the first "SEPHACRYL S-400" column were loaded onto a CsCl gradient and separated by ultracentrifugation (Details of the methods for CsCl gradient ultracentrifugation are described in Hilleman et al., J. Infection 7: Supplement I, 3–8 (1983) and Adamowicz et al., Vaccine 2: 209–214 (1984).

The results obtained using CsCl gradient separation (isopycnic banding) were: HBsAg particles of high purity (more than 90%) were recovered, but however, recovery was low (about 40–50%). This decrease in recovery is due to the necessary dialysis of HBsAg particles recovered from the CsCl gradient, where dialysis is carried out in dialysis bags to which HBsAg particles adhere. Furthermore, CsCl gradient ultracentrifugation is very expensive and time consuming and thus not industrially applicable. The preferred method is therefore that described in Example 5 and FIG. 4.

Table 2 compares applicant's preferred novel process methods of HBsAg particle purification to alternative methods employed in HBsAg particle purification. Included are possible alternative methods applicant has employed during development of his system. Details of preferred method A are provided in Example 5 and in FIG. 4. Details of alternative methods are described above in Example 10. Details of an especially preferred method (preferred method B) are provided in Example 11 and in FIG. 8.

TABLE 2

STEPS IN PRODUCTION-PURIFICATION PROCESS FOR HBsAg PARTICLES

| Possible Methods | Step 1 | Step 2 | Step 3 | Step 4 | Step 5 | *Yield (% recovery) | **Purity (%) |
|---|---|---|---|---|---|---|---|
| Preferred Method | Ultrafiltration Pre-fractionation of culture media on Pellicon ® 300,000 MW cut-off membrane | Ultrafiltration Clarification of crude media on Pellicon ® 0.22 micron cut-off membrane | Ultrafiltration Concentration of clarified media on Pellicon ® 300,000 MW cut-off membrane followed by Minitan ® 300,000 MW cut-off membrane | Gel Filtration I on Sephacryl S-400 column | Gel Filtration II on Sephacryl S-400 column | 78 | >95 |
| Alternative Method I | Culture media Pre-fractionated as in preferred method | Ultrafiltration Clarification as in preferred method | Ultrafiltration concentration as in preferred method | Gel Filtration as in preferred method | CaCl gradient (Isopycin banding ultracentrifugation | 40–50 | >90 |
| Alternative Method II | Culture media Pre-fractionated as in preferred method | Ultrafiltration Clarification as in preferred method | Ultrafiltration concentration as in preferred method | Gel Filtration as in preferred method | Sucrose gradient banding by ultracentrifugation | 70 | 60–70 |
| Alternative Method III | Culture media Pre-fractionated as in preferred method | Ultrafiltration Clarification as in preferred method | Ultrafiltration concentration as in preferred method | Gel Filtration as in preferred method | Step 5 omitted | 92 | 60–70 |
| Alternative Method IV | Culture media not pre-fractionated | Ultrafiltration Clarification as in preferred method | Ultrafiltration concentration on Pellicon ® or Amicon ® 300,00 MW cut-off membrane, followed by 10% PHG fractionation | Gel Filtration as first column Sephacryl S-400 | Gel Filtration second column Sephacryl S-400 | 95 | 60–70 |
| Alternative Method V | Culture media not pre-fractionated | Ultrafiltration Clarification as in preferred method | Ultrafiltration concentration on Pellicon ® or Amicon ® 300,00 MW cut-off membrane, followed by 10% PHG fractionation | Gel Filtration as first column Sephacryl S-400 | Gel Filtration second column Sepharose CL-6B | 60–70 | 56 |
| Alternative Method VI | Culture media not pre-fractionated | Ultrafiltration Clarification as in preferred method | Ultrafiltration concentration on Pellicon ® or Amicon ® 300,00 MW cut-off | Gel Filtration as first column Sepharose CL-68B | Gel Filtration second column Sepharose CL-6B | 70 | 30 |

TABLE 2-continued

STEPS IN PRODUCTION-PURIFICATION PROCESS FOR HBsAg PARTICLES

| Possible Methods | Step 1 | Step 2 | Step 3 | Step 4 | Step 5 | *Yield (% recovery) | **Purity (%) |
|---|---|---|---|---|---|---|---|
| Alternative Method VII | Culture media not pre-fractionated | Harvested media clarification as in preferred method | membrane, followed by 10% PHG fractionation Concentration by 10% PHG fractionation followed by centrifugation or ultrafiltration on 300,000 MW cut-off membrane | Affinity chromatography with Affi-Gel Blue ® column | No Step 5 | 10–30 | 5–7 |
| Alternative Method VIII | Culture media not pre-fractionated | Harvested media clarification as in preferred method | Concentration by 10% PHG fractionation followed by centrifugation or ultrafiltration on 300,000 MW cut-off membrane | Affinity chromatography with Blue-Sepharose ® column | No Step 5 | 10–30 | 5–7 |
| Alternative Method IX | Culture media not pre-fractionated | Harvested media clarification as in preferred method | Concentration by Ultrafiltration on 300,000 MW cut-off membrane followed by PHG fractionation 300,000 MW cut-off membrane | Affinity chromatography with Phenyl-Sepharose ® column | No Step 5 | 22 | 7 |
| Alternative Method X | Culture media not pre-fractionated | Harvested media clarification as in preferred method | Concentration by Ultrafiltration on 300,000 MW cut-off membrane followed by PHG fractionation 300,000 MW cut-off membrane | Affinity chromatography with Heparin-Sepharose ® column | No Step 5 | 10–20 | 5–7 |
| Alternative Method XI | Culture media not pre-fractionated | Harvested media clarification as in preferred method | Concentration by Ultrafiltration on 300,000 MW cut-off membrane followed by PHG fractionation 300,000 MW cut-off membrane | Affinity chromatography with DEAF-Sepharose ® column | No Step 5 | 70 | 5–10 |
| Alternative Method XII | Culture media not pre-fractionated | Clarification as in preferred method | Concentration by Ultrafiltration on 10.00 MW or 100,000 MW cut-off membrane | No Step 4 | No Step 5 | 96–100 | 0.4 |
| Alternative Method XIII | Culture media not pre-fractionated | Clarification as in preferred method | Concentration by Ultrafiltration on 300,000 MW cut-off membrane as in preferred method | No Step 4 | No Step 5 | 98 | 3–4 |
| Alternative Method XIV | Culture media not pre-fractionated | Clarification as in preferred method | Concentration by Ultrafiltration on 300,000 MW cut-off membrane followed by 10% PHG fractionation | No Step 4 | No Step 5 | 70 | 7–10 |
| Alternative | Culture media | Clarification as | Concentration by | No Step 4 | No Step 5 | 96 | 15 |

TABLE 2-continued
STEPS IN PRODUCTION-PURIFICATION PROCESS FOR HBsAg PARTICLES

| Possible Methods | Step 1 | Step 2 | Step 3 | Step 4 | Step 5 | Yield (% recovery)* | Purity (%)** |
|---|---|---|---|---|---|---|---|
| Method XV | pre-fractionated as in preferred method | in preferred method | Ultrafiltration on 300,000 MW cut-off membrane as in preferred method | | | | |
| Alternative Method XVI | Culture media not pre-fractionated | Clarification as in preferred method | Concentration by 10% PHG fractionation followed by centrifugation or Ultrafiltration on 300,000 MW cut-off membrane | No Step 4 | No Step 5 | 75 | 0.5–1 |
| Alternative Method XVII | Culture media not pre-fractionated | Clarification as in preferred method | No Step 3 | No Step 4 | No Step 5 | 100 | less than 0.4 |
| Alternative Method XVIII | Culture media pre-fractionated as in preferred method | Clarification as in preferred method | No Step 3 | No Step 4 | No Step 5 | 100 | 0.4 |
| Alternative Method XIX | Culture media pre-fractionated as in preferred method (300,000 MW cut-off membrane) | No Step 2 | No Step 3 | No Step 4 | No Step 5 | 100 | 0.4 |
| Alternative Method XX | Culture media pre-fractionated on 10,000 or 100,000 MW cut-off membrane | No Step 2 | No Step 3 | No Step 4 | No Step 5 | 0 cells did not grow well | 0 |

*Yield (% recovery) is expressed as the amount of HBsAg obtained from the final step of the process as a % of the origianl amount at the beginning of the process.
**Purity is expressed as the amount of HBsAg particles present after the final step of the process as a % of total protein obtained at this

EXAMPLE 11

Preferred Method B for Production and Purification of MBsAg Particles (Especially Preferred Method)

A. Detailed Description of the HBsAg Production-Purification Process

A flow diagram illustrating this method is depicted in FIG. 8.

Note that pyrogen-free water and vessels are used throughout all the steps.

Steps 1 through 3:

These steps are as described for steps 1 through 3 in preferred method A (Example 5).

Step 4: DNase Treatment of HBsAg Particles from Concentrated, Clarified Culture Media The 150 ml retentate (or concentrate) recovered from the Minitan ® System of Step 3 is treated with 1 vial of 11,700 units of protease-free DNase (United States Biochemical Corporation). The incubation is for 2 hours at room temperature; by this treatment the DNA content is decreased from 20 ng/μg HBsAg to 2 pg/μg HBsAg.

At the end of DNase treatment the protein solution is diluted 1:5, with 20 mM NaAc pH=4.5. The pH is adjusted (if necessary) to pH 4.5. The dilution is performed in siliconized bottles to prevent adsorption of HBsAg.

After dilution and acidification turbidity appear,.s which is removed by centrifugation on the "SOR-VALL" Centrifuge at 12,000 rpm for 30 min. The supernatant (about 850 ml) contains the HBsAg.

Note that the dilution and acidification process is done to make the solution suitable for the "TRISAC-RYL" column of Step 5, to which a low salt, low pH solution must be added. Surprisingly, the turbidity produced by these conditions contained albumin and other contaminants, but no HBsAg. Removal of this turbidity by centrigugation thus achived purification without loss of HBsAg.

Step 5: Ion-exchange Purification of HBsAg Particles After DNase Treatment

In this stage the supernatant from the centrifugation of the previous step is fed into a cation exchange column, SP-TRISACRYL LS (IBF, France). Many ion-exchange resins were tested for the purification of the HBsAg (see Section C below). Unexpectedly, SP-TRISACRYL LS cation exchange column was the only column which has a high capacity and produced both high yield and a high degree of purification; SP-Trisacryl ® LS is a copolymer of N-Acrylolyl-2-amino-2-hydroxymethyl-1.3 propane-diol which has as functional sulfonic acid group the chemical grouping:

$-CONH-C(CH_3)_2-CH_2-SO_3H.$

The column used is a 5 cm×21.5 cm column (PHARMACIA) packed with 430 ml of SP-TRISACRYL LS at a maximum linear flow velocity of 3.6 (720 ml/hr).

The column is equilibrated at the above flow rate with 5 bed volumes of 20 mM NaAc pH=4.5. After loading, the column is washed with 3 bed volumes of 50 mM NaCl in 20 mM NaAc, pH=4.5.

The eluate from the loading and washing steps (which contains DNA and DNA breakdown products) is discarded. Elution of HBsAg starts with the buffer change to 140–200 mM NaCl in 20 mM NaAc, pH =4.5. The linear flow rate in the elution step is 6.3 (1260 ml/h). Progress of the run is monitored continuously by following the absorbance of the eluate at 280 nm. Two peaks appear, the first of which contains pure HBsAg, and the second of which contains some albumin contamination, the amount of which depends on the NaCl concentration used. By this step about 80% of the HBsAg is displaced from the column in one bed volume. The first peak, containing very pure HBsAg, is collected for the next step.

Step 5A

The HBsAg eluate from the "SP-TRISACRYL" column is incubated with 1:4000 dilution of 37% formaldehyde (USP grade) for 48 hours at 30° C. This treatment inactivates possible existing viruses in the protein solution, and is performed solely as a precautionary measure.

Step 6: Concentration and Purification

The HBsAg-containing solution from the previous step is concentrated on the "MINITAN" or "PELLICON" ultrafiltration system using 100,000 MW cut-off membranes. The permeate flow rate is 1 liter/hr. HBsAg does not pass the membrane and is collected in the retentate. The retentate solution is concentrated to about 50% of its original volume.

The concentrated retentate solution is now treated as Step 4 in preferred method A. The solution is fed onto two connected 5 cm×100 cm "SEPHACRYL-400" superfine gel filtration columns, packed with a total volume of 4L resin at a flow rate of 140 ml/hr. (Alternatively one larger column may be used.)

The column is equilibrated at the above flow rate with at least 2 bed volumes of PBS buffer (Example 5).

The HBsAg elutes after the void volume, and has high purity (greater than 98%). Formaldehyde is retained on the column, and elutes after about one bed volume. Applicant believes it may be possible to omit this chromatography step on "SEPHACRYL-400" without significant loss of purification and in that case the formaldehyde is removed by diafiltration on the "MINITAN" or "PELLICON" ultrafiltration system.

The HBsAg containing eluate from "SEPHACRYL-400" column may be sterilized by filtration through a Gelman ACRO 50A (0.2 micron) filter into glass bottles.

B. Advantages of the Above Preferred Method B Over Preferred Method A (Example 5)

This new method produces a highly efficacious product which is even purer than that produced by the previous method. The purity (as regards protein) is greater than 98% and the DNA contamination is below 0.3 pg per mg HBsAg. The product is therefore of clinical grade. This new especially preferred method remains simple, involving only 5–6 steps and is rapid and very efficient. The product thus produced is of high purity at very low cost.

C. Advantages of the "SP-TRISACRYL" LS Column Used in Step 5 Over Other Ion-Exchange Columns Many columns were tested and compared for their ability to further purify the HBsAg particles after the initial purification of steps 1 through 3. "SP-TRISACRYL" proved to be the only ion-exchange resin which has the combination of having sufficient capacity for the HBsAg and also producing high yield and purity.

In order to illustrate the unexpectedness of the successful use of the "SP-TRISACRYL" column to purify HBsAg particles, a description of the use of all the columns tested follows. These results clearly show that the "SP-TRISACRYL" column has a surprising advantage over all the other columns tested.

| COLUMNS TESTED AFTER STEP 3 FOR PURIFICATION OF HBsAg PARTICLES | | |
|---|---|---|
| (a) | S-Sepharose ® | |
| | Problems: | (1) Low Recovery - high affinity to particles |
| | | (2) DNA binding and elution with particles |
| (b) | Dextran Sulphate | |
| | Problems: | (1) Very low capacity. |
| | | (2) Recovery is variable with different buffer conditions. |
| (c) | HA Ultragel | |
| | Problems: | (1) Very low capacity. |
| | | (2) Poor recovery. |
| (d) | HTP Biogel | |
| | Problems: | 50% recovery only - high affinity of HBsAg to HTP - "Biogel". |
| (e) | DEAE Sepharose | |
| | Problems: | Low capacity - recovery not measured. |
| (f) | SP-Trisacryl | |
| | Advantages: | High capacity and high recovery (yield). |

EXAMPLE 12

Seroconversion in Humans

Applicant's recombinant HBsAg vaccine (produced as described in Example 11) was injected into adult volunteers, and elicitation of a high titre of antibodies to the vaccine was demonstrated using commercial assays for anti-HBsAg antibodies, either "AUSAB EIA" or AUSAB RIA (ABBOTT).

Furthermore, a non-responder was identified, i.e., a human subject who had not responded to a previous vaccine of yeast-derived recombinant HBsAg. Injection of applicant's recombinant HBsAg vaccine elicited the production of antibodies against HBsAg. This indicates that applicant's recombinant HBsAg vaccine should produce a higher proportion of immunized subjects than currently available vaccines.

Further Evaluation of the Quality of the Antibodies Elicited in Humans

Human sera were collected from a person immunized with applicant's HBsAg vaccine and compared to human sera from a person immunized with the "RECOMBIVAX" vaccine and also from a patient suffering from hepatitis B infection. The sera were analyzed for the presence of anti-Pre-SI antibodies by a solid-phase ELISA (as described in Example 9, Section D) with the second antibody being biotinylated anti-human affinity purified IgG (Sigma, Catalog #B-9015). The results are shown below in Table 4.

TABLE 4

Results of a Solid-Phase ELISA for Anti-Pre-S1 Antibodies in Human Sera

| Source of Serum | O.D. (at 405 nm) | |
|---|---|---|
| | Experiment 1 | Experiment 2 |
| After Applicant's Vaccine | 0.556; 0.572 | 0.840; 0.843 |

TABLE 4-continued
Results of a Solid-Phase ELISA for Anti-Pre-S1 Antibodies in Human Sera

| Source of Serum | O.D. (at 405 nm) | |
|---|---|---|
| | Experiment 1 | Experiment 2 |
| Patient | 0.530; 0.538 | n.d.* |
| After Recombivax | 0.365; 0.377 | n.d.* |
| Normal Human Serum | 0.362; 0.367 | 0.389; 0.386 |

*not done

Table 4 shows that there are anti-Pre-S1 antibodies in the blood of a person immunized with applicant's vaccine, and that the levels of these antibodies are similar to those in the blood of a patient suffering from hepatitis B infection. However, the blood of a person immunized with the yeast-derived RECOMBIVAX contains no anti-Pre-S1 antibodies.

Applicant believes that this is the first time that it has been shown that a recombinant HBsAg vaccine elicits the production of anti-Pre-S1 antibodies, and these findings demonstrate that applicant's vaccine is more efficacious than existing vaccines in that it can overcome problems of non-responsiveness to the S region or Pre-S2 region determinants by having Pre-S1 determinants as well (see, for example, Zuckerman, J., Infection 13: 61-67 (1986) (Supplement A)).

EXAMPLE 13
Preferred Method C for Production and Purification of HBsAg

A. Detailed Description of the HBsAg Production-Purification Process (Preferred Method C)

A flow diagram illustrating this method is depicted in FIG. 9.

Steps 1 through 3

These steps are as described for Steps through 3 in preferred method A (Example 5) and preferred method B (Example 11).

Step 4. Purification of HBsAg Particles on DEAE Anion Exchange Column

The retentate, or concentrate, (100-400 ml) recovered from the "MINITAN" or "PELLICON" system of Step 3 is applied to an ion-exchange column containing 400-900 ml DEAE Fast Flow in suspended and equilibrated in 1×PBS (pH 7.35±0.05).

The flow-through volume is collected, the column is then washed (0.5 volume of load) with 1×PBS, and the eluate is collected and added to the flow-through volume (total volume =1.5 volumes of load).

After the DEAE column, the protein solution is diluted 1:3 with 10 mM NaAc (pH=4.5) and acidified to pH=4.5. (After this dilution there is no visible turbidity, unlike the similar process at the end of Step 4 in preferred method B; this is because almost all the albumin has been removed by the DEAE column. As a consequence of this, the centrifugation step to remove the turbidity can now be omitted.)

Note that an optional additional step is to treat the concentrate of Step 3 with DNase (as described in preferred method B, Step 4) before the DEAE chromatography step.

Step 5: Ion Exchange Purification of HBsAg Particles

In this step the diluted and acidified flow-through solution of the previous step is fed into a cation exchange column, SP TRISACRYL LS, as described in Step 5 of preferred method B (Example 11).

Step 5A: Formaldehyde Treatment

The HBsAg eluted from the SP-TRISACRYL column is treated with formaldehyde, as described in Step 5A of preferred method B (Example 11).

Step 6: Removal of Formaldehyde and Sterilization

The formaldehyde is removed from the formaldehyde-treated HBsAg solution of the last step by dialysis. The dialysis is carried out on the "MINITAN" (or "PELLICON") ultrafiltration system using 30,000 or 100,000 MW cut-off membranes. Dialysis is done against 1×PBS and the retentate is concentrated to approximately 50 ml before the start of dialysis. The dialysis is complete after 3-4 cycles of condensation and dialysis, when the retentate is concentrated to approximately 50 ml. The ultrafiltration system is washed with 1×PBS which is added to the retentate such that the total final volume of the retentate is 100 ml. This HBsAg solution is sterilized by filtration through an 0.2 micron filter and stored at 4° C.

B. Advantages of the Above Preferred Method C Over Preferred Method B (Example 11)

This new method produces a product which is of approximately the same degree of purity as the previous method (preferred method B). The yield of product is also approximately that achieved in preferred method B. Furthermore, analysis of the HBsAg particles produced by method C indicates that they are identical to those produced by method B. The advantage of this new method lies in the greater simplicity of the method which thus produces a product of very high purity at a very low cost. The method is simpler because:

(a) Replacement of the DNase step in preferred method B by a DEAE column also removes a cumbersome centrifugation step; the overall cost of the process is also reduced because the cost of the DNase is removed.

(b) The concentration step before the formaldehyde step is omitted; it is not necessary since the subsequent gel filtration step is removed.

(c) The time-consuming steps, of equilibration, running and regeneration of the SEPHACRYL column are omitted.

(d) The concentration step after the SEPHACRYL column chromatography (gel filtration) step is omitted.

C. Advantages of the DEAE Sepharose Column

This ion exchange step is believed to be a novel step in the purification of HBsAg particles. This step is novel in that the HBsAg particles do not bind nor are retarded by the column but pass straight through. Purification is achieved because the contaminants bind to or are retarded by the column; DNA binds to the column (hence the DNase step of method B may be omitted) and the major protein contaminant, albumin, is retarded by the column and elutes after the HBsAg particles. Similarly, other anionic contaminants such as proteins, charged lipids, polysaccharides and membrane fragments are separated from the HBsAg particles. Furthermore, the pH indicators (dyes) from the cell culture medium also bind to the column and are hence separated from the HBsAg particles. After this easily-performed step the purity of the HBsAg particles is greater than 90%.

Note that the DEAE column as used here has a large capacity, since the conditions (pH, ionic strength) are selected so that the particles will pass straight through the column. (This differs from the attempted use of a DEAE column described in Example 11, Section C(e), where applicant sought to achieve purification of the HBsAg particles by binding them to the DEAE column).

What is claimed is:

1. A process for producing purified, hepatitis B surface antigen particles which comprises:
   (a) culturing mammalian cells which produce the particles in a culture medium so that the cells secrete hepatitis B surface antigen particles into the culture medium, the medium being supplemented with a serum which is free of molecules having a molecular weight greater than about $3 \times 10^5$ daltons;
   (b) removing whole cells, cellular debris and particle aggregates from the resulting culture medium containing the hepatitis B surface antigen particles;
   (c) treating the resulting culture medium so as to concentrate and purify the hepatitis B surface antigen particles present therein; and
   (d) recovering the resulting concentrated, purified hepatitis B surface antigen particles.

2. A process of claim 1, wherein the hepatitis B surface antigen particles are human surface antigen particles.

3. A process of claim 1, wherein the serum of step (a) is fetal calf serum.

4. A process of claim 1, wherein the whole cells, cellular debris and particle aggregates are removed by ultrafiltration.

5. A process of claim 1, wherein the treatment in step (c) to concentrate and purify the hepatitis B surface antigen particles comprises ultrafiltration.

6. A process of claim wherein the recovery of the concentrated, purified hepatitis B surface antigen particles comprises chromatography.

7. A process of claim 6, wherein the chromatography comprises gel filtration chromatography.

8. A process of claim 7, wherein the gel filtration chromatography comprises chromatography on a column of an allyl dextran covalently cross-linked with N,N' methylene bisacrylamide.

9. A process of claim 7, wherein the gel filtration chromatography comprises chromatography on a column which excludes molecules of molecular weight greater than about $1 \times 10^6$ daltons.

10. A process of claim 7, wherein the resulting concentrated, purified hepatitis B surface antigen particles are further concentrated by ultrafiltration.

11. A process of claim 10, wherein the resulting concentrated, purified hepatitis B surface antigen particles are further purified by gel filtration chromatography.

12. A process of claim 1, wherein the treatment in step (c) to concentrate and purify the hepatitis B surface antigen particles comprises dialysis.

13. A process of claim 12, wherein the resulting concentrated, purified hepatitis B surface antigen particles are further concentrated by ultrafiltration.

14. A process of claim 1, wherein the mammalian cells comprise Chinese Hamster Ovary (CHO) cells.

15. A process of claim 14, wherein the CHO cells are CHO-HB200 cells.

16. A process for producing purified, concentrated human hepatitis B surface antigen particles which comprises:
   (a) culturing mammalian cells which produce the particles in a culture medium so that the cells secrete human hepatitis B surface antigen particles into the culture medium, the medium being supplemented with a serum which is free of molecules having a molecular weight greater than about $3 \times 10^5$ daltons;
   (b) removing whole cells, cellular debris and particle aggregates from the resulting culture medium containing the human hepatitis B surface antigen particles;
   (c) treating the resulting culture medium so as to obtain a solution containing concentrated human hepatitis B surface antigen particles;
   (d) treating the resulting solution containing concentrated antigen particles so as to decrease the DNA content of the solution;
   (e) adjusting the pH of the then-resulting solution containing concentrated and purified surface antigen particles so as to, if necessary, obtain a pH between about 3.0 and about 7.0;
   (f) purifying the concentrated surface antigen particles present within the resulting solution; and
   (g) recovering purified, concentrated human hepatitis B surface antigen particles.

17. A process of claim 16, wherein the treatment in step (d) to decrease the DNA content comprises adding DNase to the solution.

18. A process of claim 17, which further comprises subjecting the resulting solution to anion exchange chromatography.

19. A process of claim 16, wherein the treatment in step (d) to decrease the DNA content comprises subjecting the solution to anion exchange chromatography.

20. A process of claim 18 or 19, wherein the anion exchange chromatography comprises chromatography on a column of crosslinked agarose having diethylaminoethyl functional groups present thereon.

21. A process of claim 16, wherein the serum of step (a) is fetal calf serum.

22. A process of claim 16, wherein the whole cells, cellular debris and particle aggregates are removed by ultrafiltration.

23. A process of claim 16, wherein the treatment in step (c) to concentrate the human hepatitis B surface antigen particles comprises ultrafiltration.

24. A process of claim 16, wherein the recovery of the purified, concentrated human hepatitis B surface antigen particles comprises chromatography.

25. A process of claim 24, wherein the chromatography comprises gel filtration chromatography.

26. A process of claim 25, wherein the gel filtration chromatography comprises chromatography on a column of an allyl dextran covalently cross-linked with N,N' methylene bisacrylamide.

27. A process of claim 25, wherein the gel filtration chromatography comprises chromatography on a column which excludes molecules of molecular weight greater than about $1 \times 10^6$ daltons.

28. A process of claim 23, wherein the resulting concentrated human hepatitis B surface antigen particles are further concentrated by ultrafiltration.

29. A process of claim 28, wherein the resulting concentrated human hepatitis B surface antigen particles are purified by gel filtration chromatography.

30. A process of claim 16, wherein the treatment in step (c) to concentrate the human hepatitis B surface antigen particles comprises dialysis.

31. A process of claim 30, wherein the resulting concentrated human hepatitis B surface antigen particles are further concentrated by ultrafiltration.

32. A process of claim 16, wherein the adjustment of the pH of the then-resulting solution comprises subjecting the solution to centrifugation.

33. A process of claim 16, wherein the purified, concentrated human hepatitis B surface antigen particles are further purified by cation exchange chromatography.

34. A process of claim 33, wherein the cation exchange chromatography comprises strong cation exchange chromatography.

35. A process of claim 34, wherein the strong cation exchange chromatography comprises chromatography on a column having sulfonic acid functional groups present thereon.

36. A process of claim 34, wherein the strong cation exchange chromatography comprises chromatography on a column of a copolymer of N-acrylolyl-2-amino-2-hydroxymethyl-1.3 propane-diol having a —CONH—C(CH$_3$)$_2$—CH$_2$—SO$_3$H functional group present thereon.

37. A process of claim 33, wherein the resulting further purified, concentrated antigen particles are treated with formaldehyde to inactivate any live organisms and viruses present.

38. A process of claim 33, wherein the resulting further purified, concentrated antigen particles are further concentrated by ultrafiltration.

39. A process of claim 38, wherein the resulting further concentrated particles ar purified by chromatography.

40. A process of claim 39, wherein the chromatography comprises gel filtration chromatography.

41. A process of claim 40, wherein the gel filtration chromatography comprises chromatography on a column of an allyl dextran covalently cross-linked with N,N' methylene bisacrylamide.

42. A process of claim 16, wherein the mammalian cells comprise Chinese Hamster Ovary (CHO) cells.

43. A process of claim 42, wherein the CHO cells are CHO-HB200 cells.

* * * * *